(12) United States Patent
Salerno et al.

(10) Patent No.: US 11,415,655 B2
(45) Date of Patent: Aug. 16, 2022

(54) REDUCED FIELD-OF-VIEW PERFUSION IMAGING WITH HIGH SPATIOTEMPORAL RESOLUTION

(71) Applicants: UNIVERSITY OF VIRGINIA PATENT FOUNDATION, Charlottesville, VA (US); BETH ISRAEL DEACONESS MEDICAL CENTER, INC., Boston, MA (US)

(72) Inventors: Michael Salerno, Charlottesville, VA (US); Yang Yang, Charlottesville, VA (US); Li Zhao, Boston, MA (US); Xiao Chen, Charlottesville, VA (US)

(73) Assignees: UNIVERSITY OF VIRGINIA PATENT FOUNDATION, Charlottesville, VA (US); BETH ISRAEL DEACONESS MEDICAL CENTER, INC., Boston, MA (US)

( * ) Notice: Subject to any disclaimer, the term of this patent is extended or adjusted under 35 U.S.C. 154(b) by 259 days.

(21) Appl. No.: 15/606,882

(22) Filed: May 26, 2017

(65) Prior Publication Data

US 2017/0343635 A1 Nov. 30, 2017

Related U.S. Application Data

(60) Provisional application No. 62/342,700, filed on May 27, 2016.

(51) Int. Cl.
*G01R 33/56* (2006.01)
*A61B 5/026* (2006.01)
(Continued)

(52) U.S. Cl.
CPC ........ *G01R 33/5601* (2013.01); *A61B 5/0013* (2013.01); *A61B 5/0044* (2013.01);
(Continued)

(58) Field of Classification Search
CPC .......... G01R 33/5601; G01R 33/56366; G01R 33/5673; G01R 33/5602; G01R 33/4838;
(Continued)

(56) References Cited

U.S. PATENT DOCUMENTS 10,677,869 B2 * 6/2020 Ellingson ........... G01R 33/5605
10,962,617 B2 * 3/2021 Weingartner ...... G01R 33/4616
(Continued)

OTHER PUBLICATIONS

Tian J, Ahmad G, Mesubi O, Jeudy J, Dickfeld T. Three-dimensional delayed-enhanced cardiac MRI reconstructions to guide ventricular tachycardia ablations and assess ablation lesions. Circ Arrhythm Electrophysiol Apr. 1, 2012; 5(2):e31-e35. (Year: 2012).*
(Continued)

*Primary Examiner* — Ashley K Buran
*Assistant Examiner* — Amy J Shafqat
(74) *Attorney, Agent, or Firm* — Meunier Carlin & Curfman LLC

(57) ABSTRACT

Some aspects of the present disclosure relate a method for magnetic resonance imaging, which can include acquiring, by applying an imaging pulse sequence, magnetic resonance data associated with a region of interest of a subject. The imaging pulse sequence can include a plurality of RF pulses configured to generate a desired image contrast, and an outer-volume suppression (OVS) module to attenuate the signal outside the region of interest. The method can further include reconstructing, from the acquired magnetic resonance data, a plurality of reduced field of view (rFOV) magnetic resonance images corresponding to the region of interest.

26 Claims, 18 Drawing Sheets
(15 of 18 Drawing Sheet(s) Filed in Color)

(51) Int. Cl.
- A61B 5/00 (2006.01)
- G01R 33/563 (2006.01)
- G01R 33/483 (2006.01)
- G01R 33/48 (2006.01)
- G01R 33/567 (2006.01)

(52) U.S. Cl.
CPC ...... A61B 5/0263 (2013.01); G01R 33/56366 (2013.01); A61B 2576/023 (2013.01); G01R 33/4826 (2013.01); G01R 33/4838 (2013.01); G01R 33/5602 (2013.01); G01R 33/5673 (2013.01)

(58) Field of Classification Search
CPC ............ G01R 33/4826; G01R 33/3664; G01R 33/3671; G01R 33/5676; G01R 33/5611; G01R 33/56325; G01R 33/56509; G01R 33/56316; G01R 33/4818; G01R 33/4824; G01R 33/4835; A61B 5/0044; A61B 5/0013; A61B 5/0263; A61B 2576/023; A61B 5/318; G06T 2207/30048
See application file for complete search history.

(56) References Cited

U.S. PATENT DOCUMENTS

| | | | | |
|---|---|---|---|---|
| 2009/0299172 | A1* | 12/2009 | Corot | A61B 5/055 600/420 |
| 2011/0044524 | A1* | 2/2011 | Wang | G01R 33/54 382/131 |
| 2013/0278258 | A1* | 10/2013 | Smith | G01R 33/56 324/309 |
| 2014/0159723 | A1* | 6/2014 | Neji | G01R 33/483 324/309 |
| 2015/0192653 | A1* | 7/2015 | Sharif | G01R 33/56366 600/420 |
| 2015/0346304 | A1* | 12/2015 | Hu | A61B 5/055 600/411 |
| 2016/0154081 | A1* | 6/2016 | Chung | G01R 33/56563 324/309 |
| 2016/0235330 | A1* | 8/2016 | Breeuwer | A61B 8/06 |
| 2017/0035298 | A1* | 2/2017 | Contijoch | A61B 5/0044 |

OTHER PUBLICATIONS

Chen X, Salerno M, Yang Y, Epstein FH. Motion-compensated compressed sensing for dynamic contrast-enhanced MRI using regional spatiotemporal sparsity and region tracking: block low-rank sparsity with motion-guidance (BLOSM). Magn Reson Med. 2014; 72(4):1028-38.

Combettes PL, Wajs VR. Signal recovery by proximal forward-backward splitting. Multiscale Modeling & Simulation. 2005; 4(4):1168-1200.

Di Bella EV, Parker DL, Sinusas AJ. On the dark rim artifact in dynamic contrast-enhanced MRI myocardial perfusion studies. Magn Reson Med. 2005; 54(5):1295-9.

Fair MJ, Gatehouse PD, DiBella EV, Firmin DN. A review of 3D first-pass, whole-heart, myocardial perfusion cardiovascular magnetic resonance. J Cardiovasc Magn Reson. 2015; 17:68.

Greenwood JP, Maredia N, Younger JF, Brown JM, Nixon J, Everett CC, Bijsterveld P, Ridgway JP, Radjenovic A, Dickinson CJ, et al. Cardiovascular magnetic resonance and single-photon emission computed tomography for diagnosis of coronary heart disease (CE-MARC): a prospective trial. Lancet. 2012; 379(9814):453-460.

Jaarsma C, Leiner T, Bekkers SC, Crijns HJ, Wildberger JE, Nagel E, Nelemans PJ, Schalla S. Diagnostic Performance of Noninvasive Myocardial Perfusion Imaging Using Single-Photon Emission Computed Tomography, Cardiac Magnetic Resonance, and Positron Emission Tomography Imaging for the Detection of Obstructive Coronary Artery Disease a Meta-Analysis. Journal of the American College of Cardiology. 2012; 59(19):1719-1728.

Jogiya R, Kozerke S, Morton G, De Silva K, Redwood S, Perera D, Nagel E, Plein S. Validation of dynamic 3-dimensional whole heart magnetic resonance myocardial perfusion imaging against fractional flow reserve for the detection of significant coronary artery disease. J Am Coll Cardiol. 2012; 60(8):756-65.

Lipinski MJ, McVey CM, Berger JS, Kramer CM, Salerno M. Prognostic value of stress cardiac magnetic resonance imaging in patients with known or suspected coronary artery disease: a systematic review and meta-analysis. J Am Coll Cardiol. 2013; 62(9):826-38.

Luo J, Addy NO, Ingle RR, Hargreaves BA, Hu BS, Nishimura DG, Shin T. Combined outer vol. suppression and T preparation sequence for coronary angiography. Magn Reson Med. 2015, 7632-1639.

Manka R, Paetsch I, Kozerke S, Moccetti M, Hoffmann R, Schroeder J, Reith S, Schnackenburg B, Gaemperli O, Wissmann L, et al. Whole-heart dynamic three-dimensional magnetic resonance perfusion imaging for the detection of coronary artery disease defined by fractional flow reserve: determination of volumetric myocardial ischaemic burden and coronary lesion location. Eur Heart J. 2012; 33(16):2016-24.

Manka R, Wissmann L, Gebker R, Jogiya R, Motwani M, Frick M, Reinartz S, Schnackenburg B, Niemann R, Gotschy A, et al. Multicenter Evaluation of Dynamic Three-Dimensional Magnetic Resonance Myocardial Perfusion Imaging for the Detection of Coronary Artery Disease Defined by Fractional Flow Reserve. Circulation-Cardiovascular Imaging. 2015; 8(5).

Menon RG, Miller GW, Jeudy J, Rajagopalan S, Shin T. Free breathing three-dimensional late gadolinium enhancement cardiovascular magnetic resonance using outer volume suppressed projection navigators. Magn Reson Med. 2017, 1533-1543.

Mozaffarian D, Benjamin EJ, Go AS, Arnett DK, Blaha MJ, Cushman M, Das SR, de Ferranti S, Despres JP, Fullerton HJ, et al. Heart Disease and Stroke Statistics—2016 Update: A Report From the American Heart Association. Circulation. 2016 133(4):e38-e360.

Pauly J, Nishimura D, Macovski A. A k-space analysis of small-tip-angle excitation. 1989. J Magn Reson 2011; 213:544 57.

Pruessmann KP, Weiger M, Scheidegger MB, Boesiger P. Sense: sensitivity encoding for fast MRI. Magn Reson Med. 1999; 42(5):952-62.

Pruessmann, et al., Advances in sensitivity encoding with arbitrary k-space trajectories. Magnetic resonance in medicine, vol. 46, No. 4, pp. 638-651, Oct. 2001.

Salerno M, Beller GA. Noninvasive Assessment of Myocardial Perfusion. Circulation-Cardiovascular Imaging. 2009; 2(5):412-424.

Salerno M, Sica C, Kramer CM, Meyer CH. Improved first-pass spiral myocardial perfusion imaging with variable density trajectories. Magn Reson Med. 2013; 70(5):1369-79.

Salerno M, Sica CT, Kramer CM, Meyer CH. Optimization of spiral-based pulse sequences for first-pass myocardial perfusion imaging. Magn Reson Med. 2011; 65(6):1602-10.

Salerno, Michael; Taylor, Angela; Yang, Yang et al. (2014) Adenosine stress cardiovascular magnetic resonance with variable-density spiral pulse sequences accurately detects coronary artery disease: initial clinical evaluation. Circ Cardiovasc Imaging 2014; 7(4):639-46.

Schwitter J, Nanz D, Kneifel S, Bertschinger K, Buchi M, Knusel PR, Marincek B, Luscher TF, von Schulthess GK. Assessment of myocardial perfusion in coronary artery disease by magnetic resonance: a comparison with positron emission tomography and coronary angiography. Circulation 2001; 103(18):2230-5.

Smith TB, Nayak KS. Reduced field of view MRI with rapid, B1-robust outer volume suppression. Magn Reson Med 2012; 67(5):1316-23.

Staewen RS, Johnson AJ, Ross BD, Parrish T, Merkle H, Garwood M. 3-D FLASH imaging using a single surface coil and a new adiabatic pulse, BIR-4. Invest Radiol. 1990; 25(5):559-67.

Tsai CM, Nishimura DG. Reduced aliasing artifacts using variable-density k-space sampling trajectories. Magnetic Resonance in Medicine. 2000; 43(3):452-458.

(56) References Cited

OTHER PUBLICATIONS

Walsh DO, Gmitro AF, Marcellin MW. Adaptive reconstruction of phased array MR imagery. Magnetic Resonance in Medicine. 2000; 43(5):682-690.

Yang Y, Kramer CM, Shaw PW, Meyer CH, Salerno M. First-pass myocardial perfusion imaging with whole-heart coverage using L1-SPIRiT accelerated variable density spiral trajectories. Magn Reson Med. 2015.

Coelho-Filho, et al., MR Myocardial Perfusion Imaging, Radiology, vol. 266: No. 3, 701-715 (2013).

Wilke, N., et al., Concepts of Myocardial Perfusion Imaging in Magnetic Resonance Imaging, Magnetic Resonance Quarterly, vol. 10, No. 4, pp. 249-286 (1994).

* cited by examiner

REDUCED FIELD-OF-VIEW PERFUSION IMAGING WITH HIGH SPATIOTEMPORAL RESOLUTION

CROSS-REFERENCE TO RELATED APPLICATION

This application claims priority to and benefit of U.S. Provisional Patent Application No. 62/342,700, filed May 27, 2016, which is hereby incorporated by reference herein in its entirety as if fully set forth below.

STATEMENT REGARDING FEDERALLY SPONSORED RESEARCH

This invention was made with government support under grants K23 HL112910 and T32 EB003841, awarded by the National Institutes of Health. The government has certain rights in the invention.

BACKGROUND

In the U.S. alone, over 8.2 million people suffer from angina pectoris, resulting in the performance of nearly 10 million stress tests annually to evaluate for the presence of coronary artery disease (CAD) ([1]). Adenosine stress perfusion cardiac magnetic resonance (CMR) has emerged as a technique with high diagnostic and prognostic utility in the evaluation of CAD ([2]-[5]). Currently available CMR perfusion imaging techniques still suffer from limitations, including dark-rim artifacts ([6]) resulting from cardiac motion and Gibbs ringing at high-contrast interfaces and limited spatial coverage of the ventricle, both of which are related to temporal footprint of the acquisition and the limited time available for data acquisition in each heartbeat. Recent 3D techniques have addressed the issue of spatial coverage of the ventricle and have demonstrated clinical utility in multi-center studies ([7]-[9]). However, these techniques have a relatively long temporal footprint which limits in-plane spatial resolutions ([10]).

First-pass contrast-enhanced myocardial perfusion CMR has proven to be a powerful noninvasive technique for evaluating coronary artery disease (CAD) ([11], [12]). Some current techniques image a limited number of 2D slices, such that small but clinically relevant perfusion defects may be missed. Rapid 2D imaging techniques can enable whole heart coverage but do so at the expense of a reduction in SNR due to the need for high acceleration. 3D perfusion imaging can be advantageous for quantifying ischemic burden by covering the whole ventricle at the same cardiac phase, but existing approaches can have limited spatiotemporal resolution.

Spiral pulse sequences demonstrate reduced motion-induced dark-rim artifacts and can accurately detect obstructive CAD as defined by quantitative coronary angiography ([12]-[14]). Given the high acquisition efficiency of spiral techniques, whole-heart coverage with a 3-interleaved spiral pulse sequence capable of imaging 8 slices with a 2 mm in-plane resolution with a temporal resolution footprint of 35 ms per slice ([15]) has been demonstrated. However, the need for multiple interleaves necessitates the use of a flip angle of around 30°, and each interleave traverses the center of k-space at a separate time relative to the saturation pulse. The feasibility of acquiring a complete perfusion image following a single RF excitation has been determined. This single-shot excitation approach acquires data with a very short temporal footprint due to the high sampling efficiency but also requires highly accelerated spiral trajectories with an associated SNR penalty which can be mitigated using a 90-degree excitation pulse.

Although the heart only occupies a small region of the chest, an imaging field of view (FOV) that encompasses the whole chest is required to avoid spatial aliasing that results from violation of the Nyquist sampling rate. For spiral imaging, where the readout direction is continually changing, a traditional anti-aliasing filter, which can be used to restrict the FOV in the RO direction, cannot be utilized and the full extent of the object must be supported in all directions to avoid aliasing.

It is with respect to these and other considerations that the various aspects of the present disclosure as described below are presented.

SUMMARY

Some aspects of the present disclosure relate to reduced field-of-view (rFOV) magnetic resonance imaging. In one aspect, the present disclosure relates to a method for magnetic resonance imaging which, in one embodiment, includes acquiring, by applying an imaging pulse sequence, magnetic resonance data associated with a region of interest of a subject. The imaging pulse sequence includes a plurality of RF pulses configured to generate a desired image contrast, and an outer-volume suppression (OVS) module to attenuate the signal outside the region of interest. The method also includes reconstructing, from the acquired magnetic resonance data, a plurality of reduced field of view (rFOV) magnetic resonance images corresponding to the region of interest.

In some embodiments, the imaging pulse sequence can be configured as a rFOV perfusion imaging sequence. In some embodiments, the imaging pulse sequence is configured as an outer-volume suppressed 3D stack-of-spirals (SOS) perfusion imaging sequence. In other embodiments, the outer-volume suppression includes outer-volume suppression for single-shot or interleaved 2D spiral perfusion imaging.

In some embodiments, the magnetic resonance data is acquired along a Cartesian trajectory, radial trajectory, echo-planar trajectory, spiral trajectory, or 2D or 3D variant thereof. In some embodiments, the imaging pulse sequence is spin-echo based, gradient-echo based, or a combination thereof. In other embodiments, image contrast can be made sensitive to T1, T2, or a combination thereof.

Another aspect of the present disclosure relates to a method for magnetic resonance imaging which, in one embodiment, includes introducing a T1-reducing contrast agent to a subject and generating a plurality of magnetic resonance images associated with a region of interest of the subject. The magnetic resonance images associated with the region of interest are generated by performing functions that include: generating T1 image contrast using a saturation pulse, an inversion pulse, or a plurality of RF pulses; applying a plurality of RF pulses such as to suppress a signal outside of the region of interest; and using a 2D or 3D readout module to acquire magnetic resonance data associated with the subject.

In some embodiments, the method can further include applying additional RF-pulses to selectively suppress a fat signal or excite a water signal associated with the subject. The additional RF-pulses can include spatial-spectral selective pulses.

In some embodiments, an RF pulse is used to only excite the signal within the region of interest. In some embodiments, an RF pulse excites or suppresses a cylindrical, rectangular, or arbitrary region of interest. In some embodiments, multiple slices can be excited simultaneously during the readout module.

In some embodiments, the method can further include the use of a contrast agent which affects T2 or T2*. In some embodiments, the preparation RF module is made sensitive to T2 or a combination of T1s and T2s. In other embodiments, the preparation RF module can be made sensitive to diffusion or myocardial motion. In other embodiments, the preparation RF module can be made sensitive to magnetization transfer or chemical exchange.

Another aspect of the present disclosure relates to a system for magnetic resonance imaging. In one embodiment, the system includes a data acquisition device configured to acquire magnetic resonance data associated with a region of interest of a subject, wherein acquiring the magnetic resonance data includes applying an imaging pulse sequence that includes: a plurality of RF pulses configured to generate a desired image contrast, and an outer-volume suppression (OVS) module to attenuate the signal outside the region of interest. The system further includes one or more processors coupled to the data acquisition device and configured to cause the system to perform functions that include reconstructing, from the acquired magnetic resonance data, a plurality of reduced field of view (rFOV) magnetic resonance images corresponding to the region of interest.

Another aspect of the present disclosure relates to a system for magnetic resonance imaging which, in one embodiment, includes: a contrast agent source configured to introduce a T1-reducing contrast agent to a subject; and a data acquisition device and one or more processors configured to cause the system to generate a plurality of magnetic resonance images associated with a region of interest. The magnetic resonance images associated with the region of interest are generated by performing functions that include: generating T1 image contrast using a saturation pulse, an inversion pulse, or a plurality of RF pulses; applying a plurality of RF pulses such as to suppress a signal outside of the region of interest; and using a 2D or 3D readout module to acquire magnetic resonance data associated with the subject.

BRIEF DESCRIPTION OF THE DRAWINGS

Reference will now be made to the accompanying drawings, which are not necessarily drawn to scale. The patent or application file contains at least one drawing executed in color. Copies of this patent or patent application publication with color drawing(s) will be provided by the Office upon request and payment of the necessary fee.

DETAILED DESCRIPTION

Figure 1:
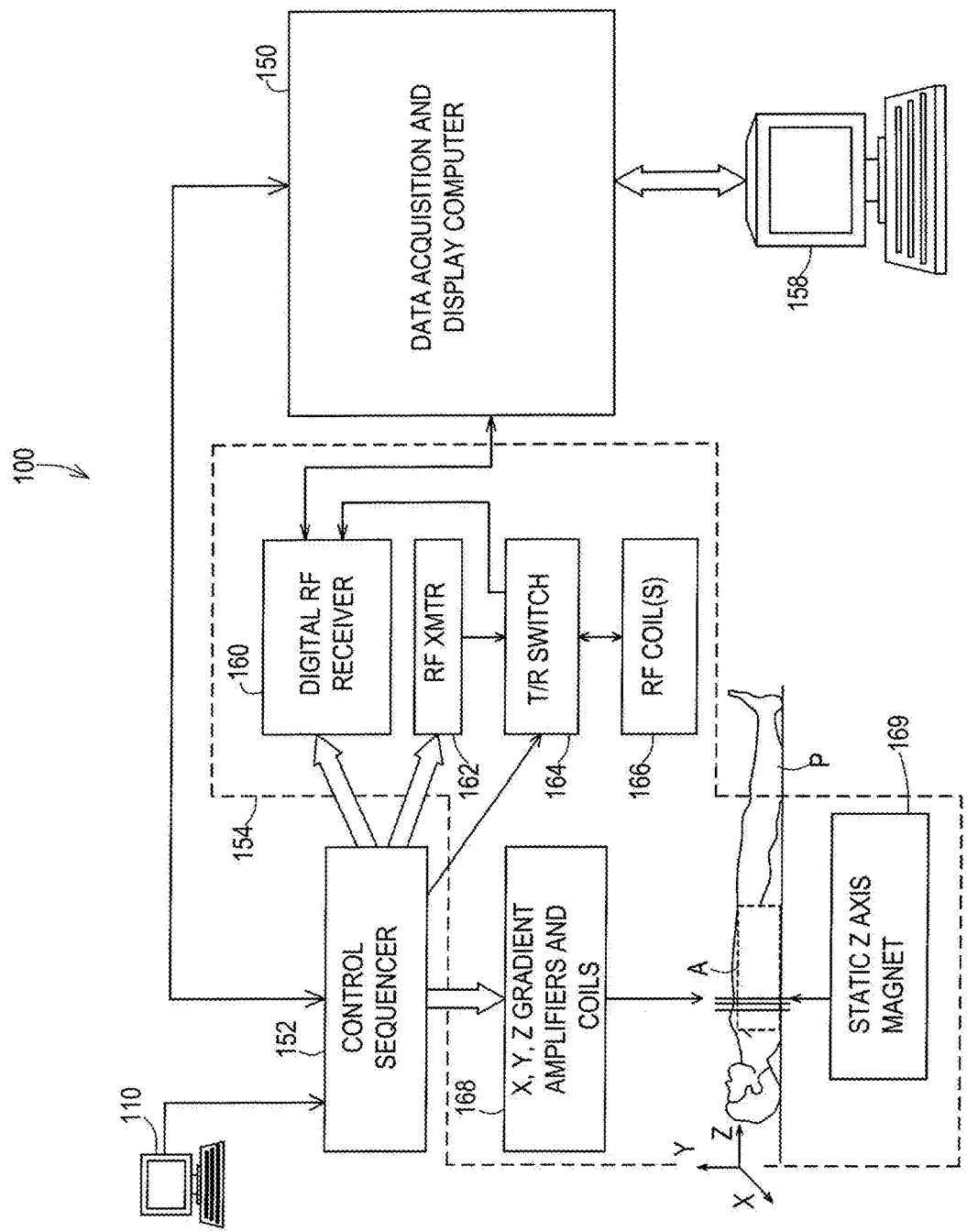
FIG. 1 is a system diagram illustrating an imaging system capable of implementing aspects of the present disclosure in accordance with one or more embodiments.

Some aspects of the present disclosure relate to reduced field-of-view (rFOV) perfusion imaging. Although example embodiments of the present disclosure are explained in detail herein, it is to be understood that other embodiments are contemplated. For example, the general approach of performing first-pass perfusion imaging with a reduced FOV is broadly applicable to rFOV pulse designs and readout modules other than those discussed with respect to specific embodiments herein. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific tissues organs, tissues, or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example to implement magnetic resonance imaging sequences in accordance with various embodiments of the present disclosure. A contrast-enhanced image of an area of interest A of the subject P (which may also be referred to herein as a "region of interest") may be shown on display 158. The display 158 may be implemented through a variety of output interfaces, including a monitor, printer, or data storage.

The area of interest A corresponds to a region associated with one or more physiological activities in subject P. The area of interest shown in the example embodiment of FIG. 1 corresponds to a chest region of subject P, but it should be appreciated that the area of interest for purposes of implementing various aspects of the disclosure presented herein is not limited to the chest area. It should be recognized and appreciated that the area of interest in various embodiments may encompass various areas of subject P associated with various physiological characteristics, such as, but not limited to the heart region, brain region, upper or lower extremities, or other organs or tissues. Physiological activities that may be evaluated by methods and systems in accordance with various embodiments of the present disclosure may include, but are not limited to, diagnosis of cardiac disease, including assessment of coronary artery disease, and, in some instances, may also relate to aspects of fluid flow and/or muscular or other organ movement or other conditions.

It should be appreciated that any number and type of computer-based medical imaging systems or components, including various types of commercially available medical imaging systems and components, may be used to practice certain aspects of the present disclosure. Systems as described herein with respect to various example embodiments are not intended to be specifically limited to the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
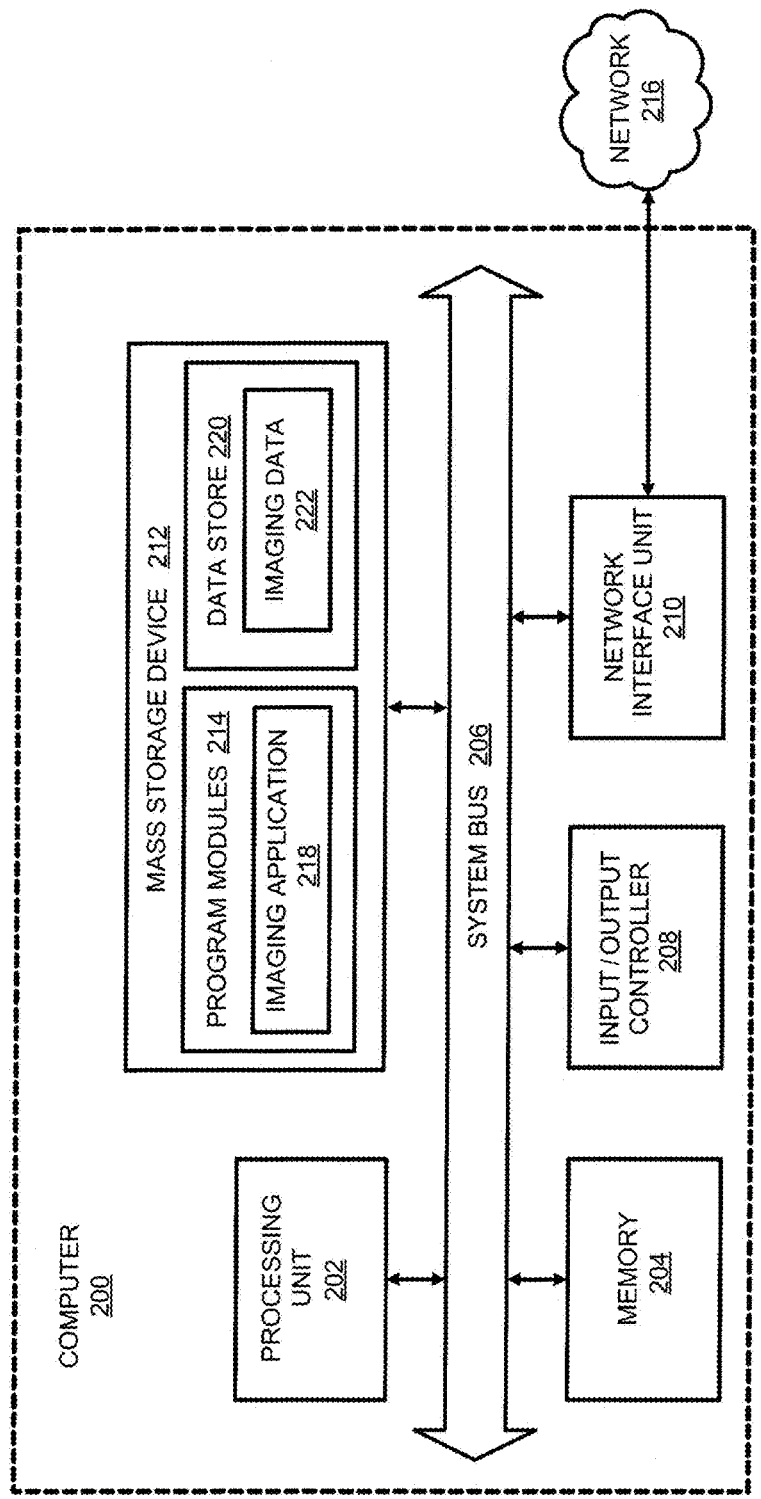
FIG. 2 is a computer architecture diagram showing a general computing system capable of implementing aspects of the present disclosure in accordance with one or more embodiments.

FIG. 2 is a computer architecture diagram showing a general computing system capable of implementing aspects of the present disclosure in accordance with one or more embodiments described herein. A computer 200 may be configured to perform one or more functions associated with embodiments illustrated in one or more of FIGS. 3-16. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 3-16 discussed below. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging pulse sequences in accordance with various embodiments of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more embodiments illustrated in FIGS. 3-16. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Some aspects of the present disclosure relate to reduced field-of-view (rFOV) magnetic resonance imaging with outer-volume suppression (OVS). In some embodiments, the rFOV magnetic resonance imaging can be applied to perfusion imaging. For instance, some disclosed embodiments relate to rFOV perfusion imaging with 2D OVS for single-shot 2D spiral perfusion imaging. Through outer-volume suppression (OVS), k-space can be sampled more coarsely ([16]), and OVS can be used for cardiac imaging ([17]). Considering the heart only occupies a small portion of the chest, rFOV perfusion imaging with 2D OVS can improve sampling efficiency ([18]).

Other embodiments can relate to perfusion imaging using an outer-volume suppressed 3D stack-of-spirals (SoS) perfusion sequence with motion-guided compressed sensing reconstruction. Implementation of certain aspects of 3D SoS perfusion sequences in accordance with some embodiments can reduce the temporal footprint while increasing the in-plane and through-plane spatial resolution as compared to previous 3D approaches.

In some embodiments, the method for magnetic resonance imaging of a subject can include generating a desired image contrast via a plurality of RF pulses. For instance, in some aspects, the method can include introducing a T1-reducing contrast agent to the subject (e.g., via IV), and generating MRI images associated with the subject. Generating the MRI images can include generating T1 image contrast using a saturation pulse or inversion pulse or plurality of RF pulses, applying a single RF pulse or plurality of RF pulses such to suppress signal outside of a desired region of interest, and using a 2D or 3D readout module to acquire image data for the MRI images. In some embodiments the image contrast can be made sensitive to T1, T2, or a combination thereof.

In some embodiments, the method for magnetic resonance imaging can include an OVS module configured to attenuate the signal outside of the region of interest. For instance, the OVS module can comprise OVS for single-shot or interleaved 2D spiral perfusion imaging. In some embodiments, the OVS module can be configured to excite the signal within the region of interest.

In another embodiment, a system is configured for performing the method for magnetic resonance imaging of the subject as described above. In yet another embodiment, a non-transitory computer-readable medium stores instructions which, when executed by one or more processors, cause a computer to perform one or more of the steps of the method for magnetic resonance imaging of the subject as described above.

In some embodiments, additional RF-pulses can be used to selectively suppress fat signal or excite a water signal. The additional RF-pulses can be spatial-spectral selective pulses. In some embodiments, an RF pulse can be used to only excite the signal within the region of interest and not to suppress signal outside of the field of view. In some embodiments, an RF pulse can excite or suppress a cylindrical, rectangular, or arbitrary region of interest.

In some embodiments, the readout module can be gradient echo-based, spin echo-based, or gradient and spin echo-based. The readout module can include echo-train based variants of the gradient echo-based, spin-echo based, and/or gradient and spin echo-based techniques. In some embodiments, k-space can be acquired along a Cartesian trajectory, radial trajectory, echo-planar trajectory, spiral trajectory, or other suitable k-space trajectory. The magnetic resonance data acquisition can include 2D and 3D variants.

In some embodiments, multiple slices are excited simultaneously (SMS) during the readout module. In some embodiments, a contrast agent which affects T2 or T2* can be used.

Design Considerations

First-pass myocardial perfusion imaging including accelerated spirals with an optimized trajectory and k-t sampling pattern can be used to produce high-quality 2D perfusion images with whole-heart coverage at heart rates up to 125 BPM ([15]). In some embodiments this technique can use multiple spiral interleaves with an effective acceleration factor of 5 to achieve whole-heart coverage with 8 slices and in-plane resolution of 2 mm by supporting a 340 mm$^2$ FOV. Additionally, in some embodiments, the temporal footprint of each perfusion image can be 35 ms. The delay time between saturation and data acquisition can be used to perform OVS to reduce aliasing from objects outside of the desired rFOV. When combined with a single-shot spiral readout, this OVS preparation can then enable perfusion imaging with the same in-plane resolution as described above but with a temporal acquisition footprint of <10 ms/slice.

Single-Shot Excitation and SNR Consideration

The balance between spatial resolution, temporal footprint, and SNR can be expressed as follows:

$$SNR \propto \eta * \delta_{xyz} * \sqrt{T_{\text{total}}} * C \qquad (1)$$

where $\eta$ is the SNR efficiency of variable-density spiral trajectory ([19]), $\delta_{xyz}$ is the spatial resolution, $T_{total}$ is the total readout time for specific slice, and C is a constant which depends on the proton density, relaxation times (T1 and T2*), and sequence parameters. In an example embodiment, 3 spirals with a 5 ms readout duration per interleaf (total readout duration 15 ms) can be used. By increasing the readout to 8 ms, the maximal duration which produces high-quality perfusion images at 1.5 T with minimal dropout and off-resonance artifacts as shown previously ([14]), SNR would still reduce to 73% as compared to the multi-shot spiral acquisition, assuming that other sequence parameters are held constant. While the single-shot sequence may have lower SNR due to the shorter total readout, as only one excitation is needed per image, in some embodiments, a 90° flip angle can be used to recover SNR. In an example embodiment, like that described above, 3 interleaved spiral, the optimal flip angle for constant magnetization with interleaved acquisition can be 31 degrees ([15]). This difference in FA can result in a 94% increase in SNR)))(sin(90°/sin(31° for the single-shot sequence with 90° excitation. The last factor to consider is the trajectory factor ($\eta$) which describes the relative loss of SNR due to non-uniform weighting of noise in k-space resulting from variable density sampling and density compensation. In an example embodiment, this factor was 0.8 for the single-shot technique as compared to the 3-interleaved sequence. Combining these factors, the single-shot technique can be advantageous as it can have raw data with an SNR that is 13% higher than that of the 3-interleaved pulse sequence, while reducing the temporal footprint from 35 ms per image to 10 ms per interleave. Notably, the single-shot trajectory requires a 12× undersampling of the outer region of k-space to achieve the same 2-mm spatial resolution, at a FOV of 340 mm$^2$. By using OVS, the effective undersampling of k-space can be reduced by a factor of 2, which reduces aliasing and should result in improved CS reconstruction as compared to the single-shot full FOV technique.

OVS Design

Figure 3:
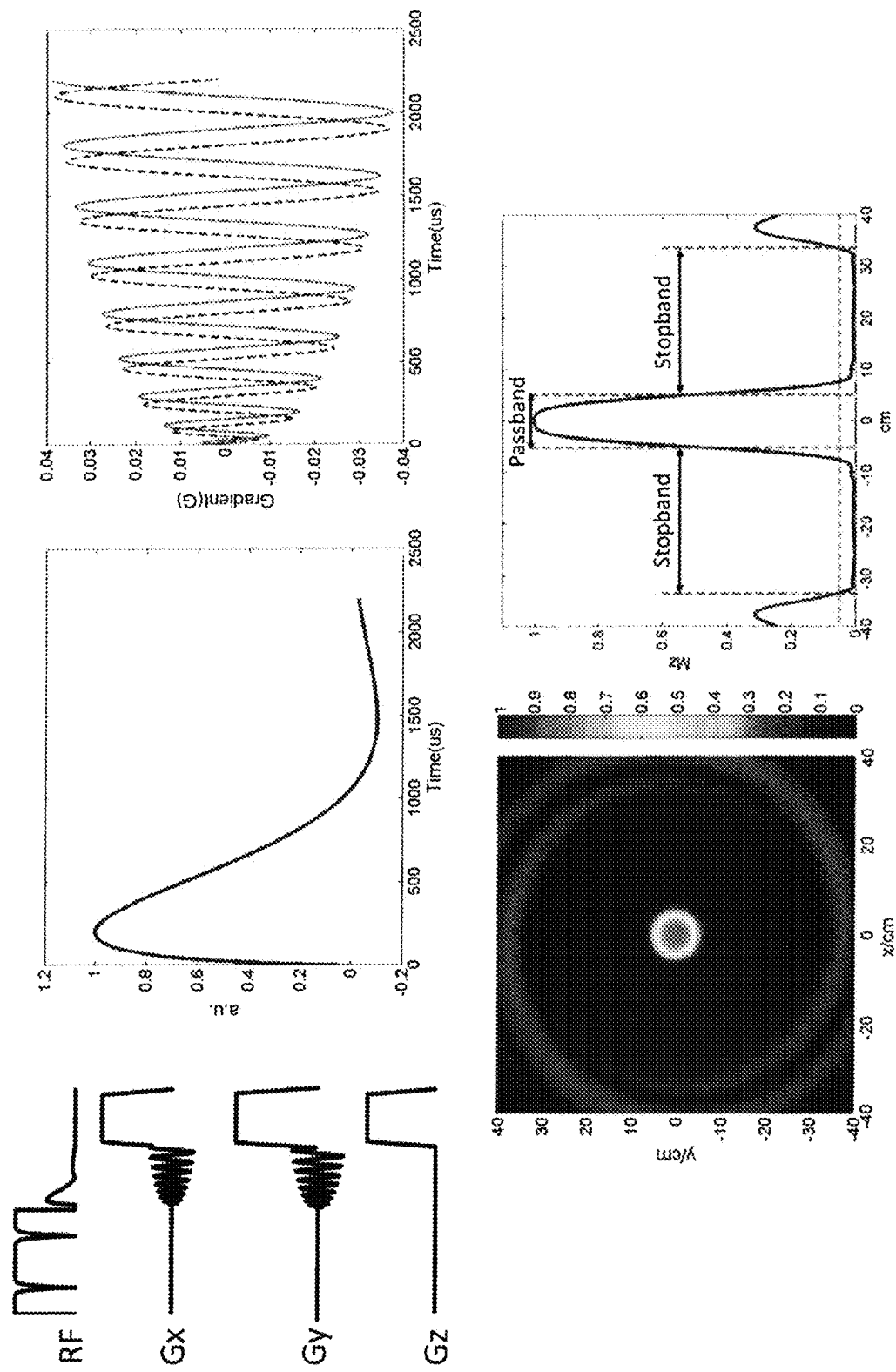
FIG. 3 shows: a diagram of the 2D OVS pulse sequence, which is comprised of a non-selective adiabatic BIR-4 tip-down pulse, the B1 profile of the RF pulse, the spiral gradient waveform of the RF pulse 2D spiral spatial selective tip-back pulse and the spoiler to crush the residual signal; a 2D spatial profile of the rFOV=100 mm design; and a 1D spatial profile across the 2D profile center to show the stopband is around ±335 mm in accordance with one or more embodiments.

Embodiments of the present disclosure can include a rapid, $B_1$-robust 2D OVS technique to enable imaging of a reduced FOV that only includes the heart. In an embodiment, as illustrated at FIG. 3, the preparation can comprise a non-selective tip-down, followed by spatially selective tip-back and a spoiler. For instance, a 4 ms adiabatic BIR-4 ([20]) tip-down pulse can be used for non-selective excitation, and a 2.2 ms jinc-shaped 2D spiral spatial selective 19 pulse with a time-bandwidth product of 4 can be used to tip back spins within a 100 mm cylindrical rFOV. The pulse was designed with a resolution of 100 mm and an excitation FOV of 800 mm (±400 mm). A 2 ms spoiler gradient can be used to dephase residual transverse magnetization. In some embodiments, the rFOV can be designed to be large enough to encompass the heart even in the presence of respiratory motion. In some embodiments, the excitation FOV can be designed to be large enough that the first spatial side-lobe may be outside of the body.

Pulse Sequence Design

Figure 4A:
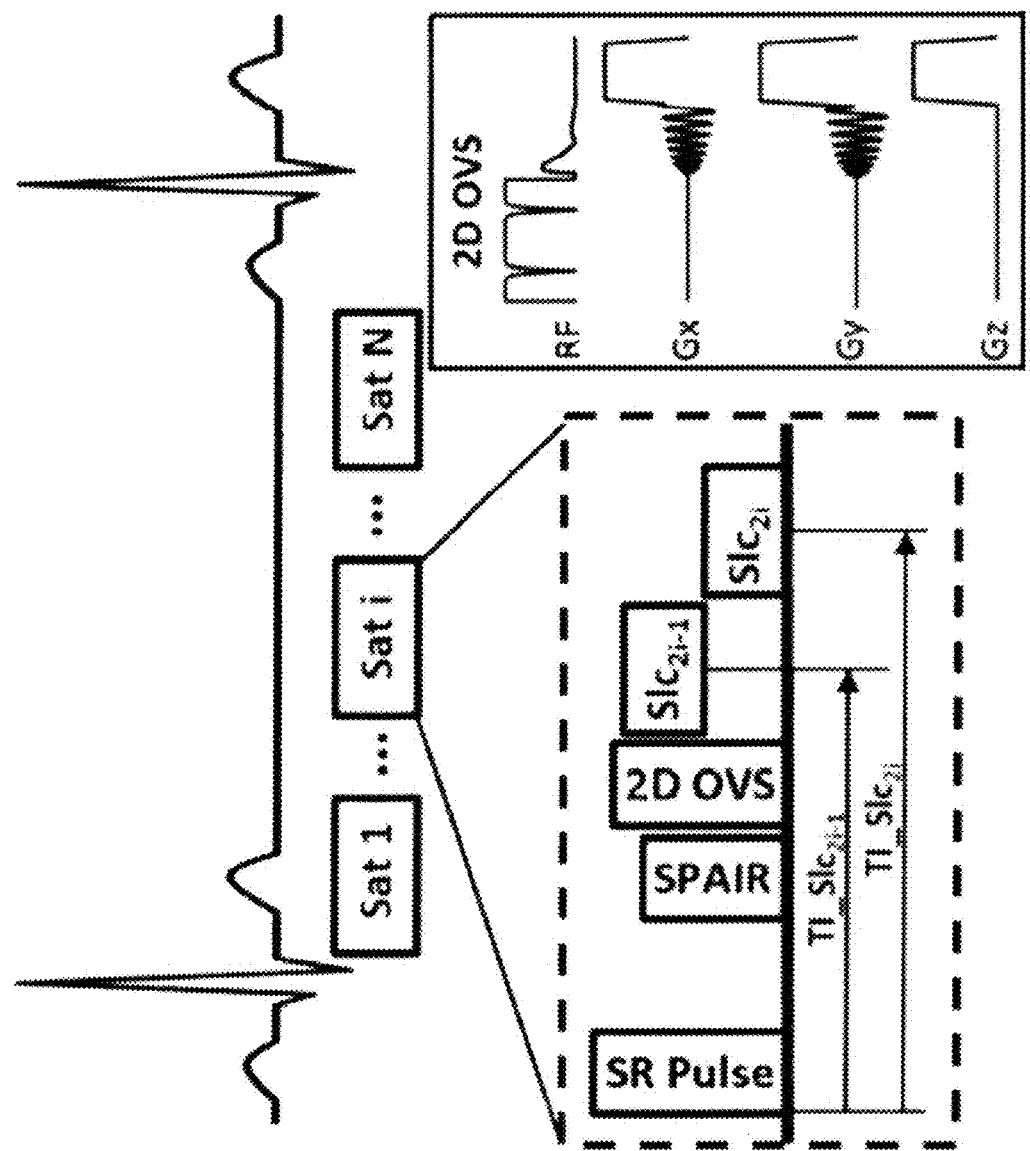
FIGS. 4*a*-4*c* show: a schematic of single-shot spiral perfusion with a 2D OVS pulse sequence (FIG. 4*a*); a k-space trajectory of the single-shot spiral with Fermi-shape dual density design (FIG. 4*b*); and a corresponding point spread function to show the incoherent sampling pattern (FIG. 4*c*) in accordance with one or more embodiments.

FIG. 4a is a schematic of single-shot spiral perfusion with a 2D OVS pulse sequence. Non-selective saturation with an adiabatic BIR-4 pulse is applied for $T_1$-weighted preparation. A spectrally selective fat-saturation (SPAIR) pulse is used to achieve fat suppression, followed by the OVS module to suppress signals from outside the heart. The SPAR pulse can be applied at a time for which fat is nulled by the combination of the BIR-4 saturation and SPAR pulse at the time of spiral acquisition of the first slice.

For each slice location, a single-shot spiral readout is acquired with a single 90-degree excitation pulse. In some embodiments, 2 slices can be acquired in each SR block with the acquisition order shown in FIG. 4a, and SR blocks can be repeated until all the slices are imaged.

Figure 4C:
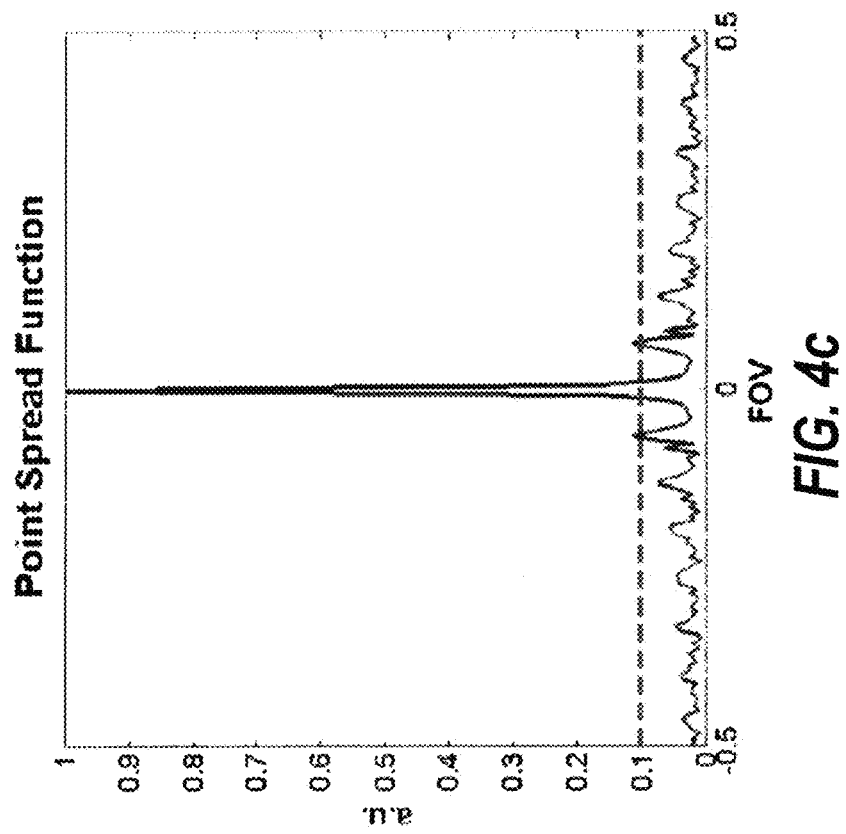
Figure 4B:
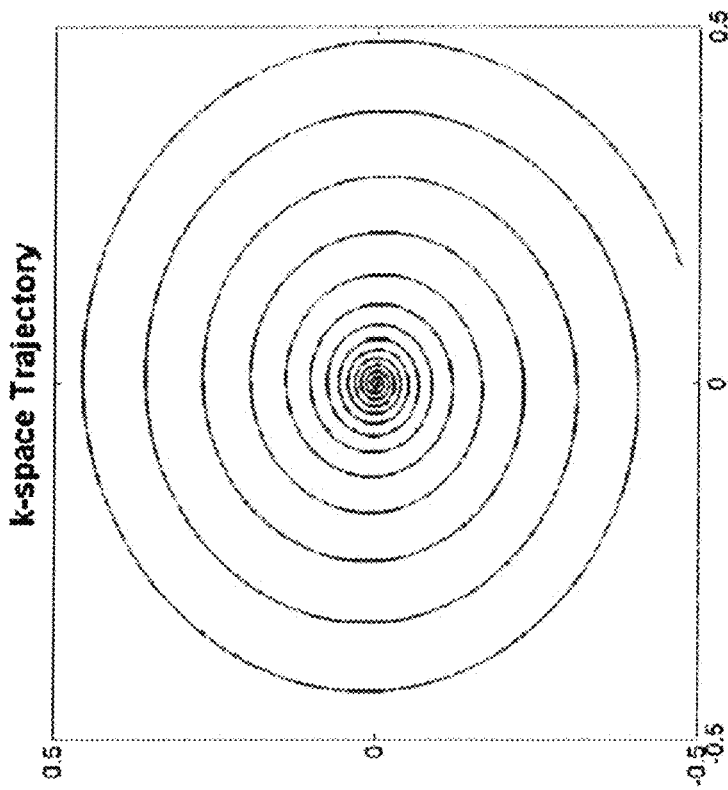

The single-shot spiral trajectory is presented in FIG. 4b. It is an 8 ms constant-slew spiral using a Fermi-shape dual density design ([15]), with 20% of the center fully sampled (in time along the trajectory) and a broad transition to reach the ending density of 0.15× Nyquist, achieving 2 mm resolution at a reduced FOV of 170 mm. The slew rate for the spiral was 120 T/m/s and the spiral achieves a maximal gradient strength of 25 mT/m at the end of the spiral trajectory.

The corresponding point spread function (PSF) is shown in FIG. 4c. The PSF has a low first side-lobe amplitude, and the side-lobe energy is distributed over a number of low amplitude side-lobes resulting from the variable density sampling strategy. When combined with rotation by the golden angle (111.25°) in time, this strategy produces a relatively incoherent and noise-like aliasing pattern well-suited to CS reconstruction.

Image Reconstruction

Block low-rank sparsity with motion-guidance (BLOSM) ([21]) combined with SENSE ([22]) can be implemented to reconstruct the under-sampled perfusion images through optimization of:

$$\text{minimize}_{m,R} \|\Phi_R m\|_{p*} s.t. \|F_u S_m - d\|_2 < E \quad (2)$$

where m represents the estimated perfusion images, d is the acquired under-sampled k-space data, and $F_u$ is the under-sampled non-uniform Fourier transform, which only takes values at the k-space positions where d can be acquired. S is the coil sensitivity map, which is estimated using eigen-analysis ([23]) from temporal average images. $\Phi_R$ represents the operator for block tracking and creation of rearranged clusters, after m is divided into blocks which are tracked using displacement maps R. $\|*\|_{p*}$ is a joint Schatten p-norm that exploits the regional low rank property. A solution to Equation 2 can be obtained by solving an unconstrained Lagrangian problem using an iterative soft-thresholding (IST) algorithm ([24]). In some embodiments, the image reconstruction can be implemented in MATLAB (R2013b, the MathWorks, Natick, Mass.).

Example Implementations and Results

Various aspects of the present disclosure will now be described with reference to some example implementations and corresponding results, and the images of FIGS. 5-16. Some experimental data are presented herein for purposes of illustration and should not be construed as limiting the scope of the present disclosure in any way or excluding any alternative or additional embodiments.

Example 1

An implementation of certain aspects of the present disclosure and discussion of corresponding results will now be described with reference to FIGS. 5-10.

Methods

OVS Evaluation

The two-dimensional spatial profile of the module was evaluated using a Bloch simulation. To evaluate the performance of the OVS module as a function of B0 and B1 inhomogeneity, Bloch simulations were performed of the module over a range of B0 (±300 Hz) and B1 scale factors of 0.2 to 1.2. Bloch equations were performed using a T1 of 300 ms and a T2 of 50 ms.

To test the OVS module performance, three Siemens QA water phantoms with short T1 (100 ms) were scanned by a Cartesian fast low angle shot (FLASH) sequence and the proposed spiral sequence with and without OVS module. The FLASH sequence parameters included: echo time (TE) 1.2 ms, repetition time (TR) 1 s, FA 15°, matrix size 128×128, slice thickness 10 mm with FOV 170 mm. Spiral pulse sequence parameters are as described below in the "Pulse Sequence Design" section.

Human Studies

To compare the performance of the full FOV and rFOV perfusion sequence, resting first-pass perfusion was performed in 16 subjects (8 for each sequence) undergoing clinically ordered CMR studies. The indications for the clinical CMR studies included evaluation of myocardial viability (N=4), pericardial disease (N=4), arrhythmias (premature ventricular contractions/ventricular tachycardia) (N=3), cardiac sarcoid (N=3), hypertrophic cardiomyopathy (N=1), and right ventricular enlargement (N=1). Imaging was performed on a 1.5 T MRI scanner (MAGNETOM Avanto, Siemens Medical Solutions, Erlangen, Germany). Perfusion imaging was performed using 0.075 mmol/kg Gd-DTPA (Bayer AG, Leverkusen, Germany) injected intravenously at a rate of 4 mL/s followed by 25 mL of saline flush at 4 mL/s. The subjects were asked to hold their breath as long as possible followed by shallow breathing during the acquisition of perfusion images over 50-60 heart beats. A 32-channel cardiac phased-array receiver coil (Invivo Corporation, Best, Netherlands) was used for signal reception. Imaging protocols for the full FOV and rFOV sequence are shown in Table 1.

TABLE 1

|  | Full FOV (N = 8) | rFOV (N = 8) |
|---|---|---|
| FOV (mm) | 340 | 170 |
| Resolution (mm) | 2.0 | 2.0 |
| Starting density | 1.2 | 1.2 |
| Ending density | 0.08 | 0.15 |
| Fully sample k-space center | 20% | 20% |

Common sequence parameters included: echo time (TE) 1.0 ms, repetition time (TR) 9 ms, saturation recovery time (SRT) 80 ms, FA 90°, temporal footprint 8 ms each slice, 2 slices per saturation, slice thickness 10 mm with no gap between slices, and 8 slices covering the whole left ventricle.

Image Analysis

Perfusion images were reconstructed by the proposed BLOSM algorithm. Image quality was graded on a 5-point scale (1-excellent, 5-poor) independently by two experienced cardiologists blinded to acquisition method by zooming in the full FOV images to the same size of rFOV images. Statistical analysis on the image scores from the two reviewers were analyzed using the Wilcoxon signed rank tests. Image quality of the full FOV and rFOV sequence was analyzed using the Mann-Whitney U test.

Results

Simulation and Phantom Results

Figure 5:
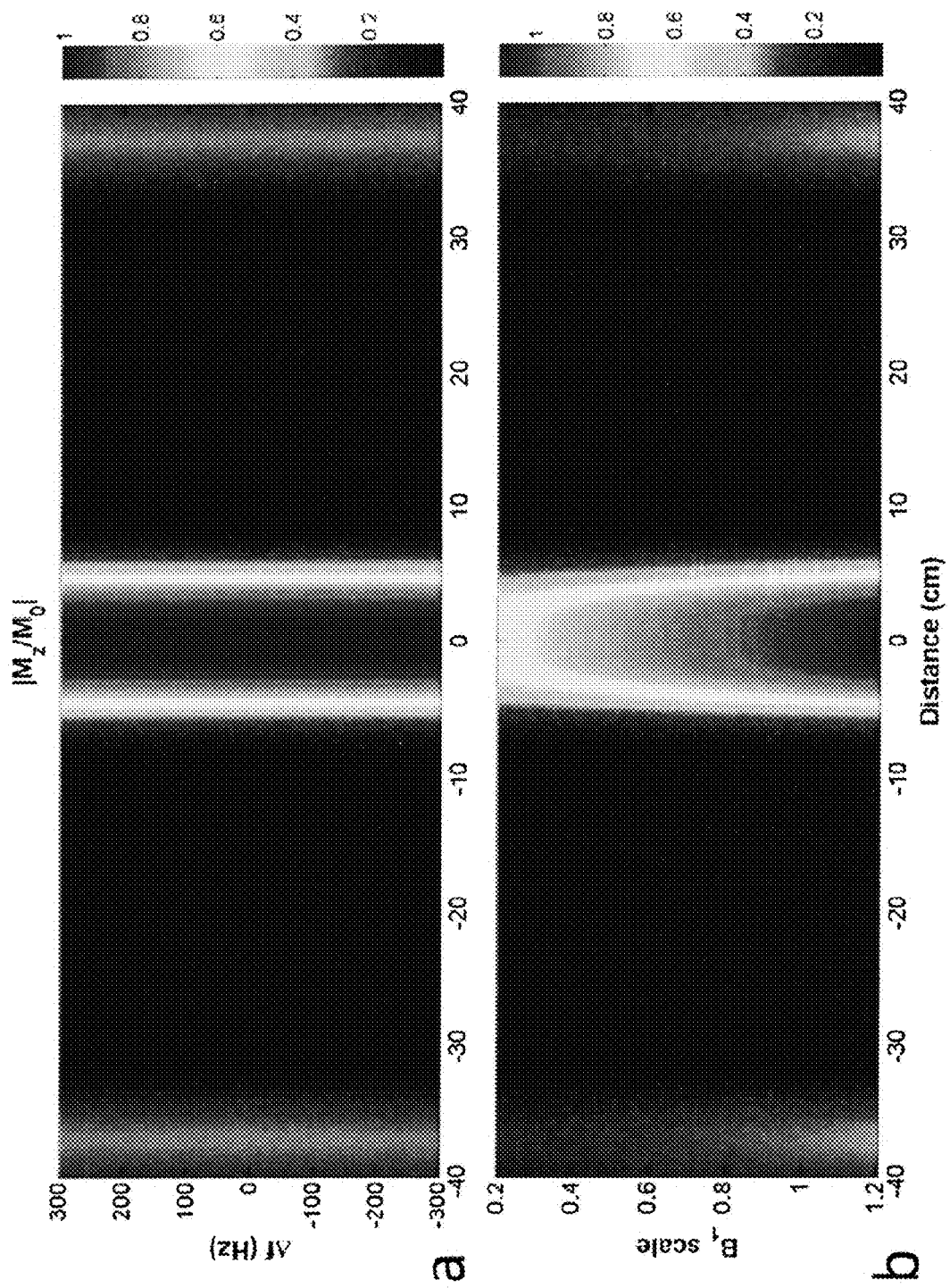
FIG. 5 illustrates simulated performances of the OVS by varying the off-resonance (a) and $B_1$ scale (b) in accordance with one or more embodiments.

The 2D spatial profile of the spiral tip-back pulse is shown in FIG. 3b and a profile along the y-axis of the pulse is shown in FIG. 3c. The FWHM of the rFOV pulse was 100 mm and the usable stopband (defined as where Mz is <5% of M0) was ±335 mm. FIG. 5 shows the simulated performance of the OVS module across the $B_1$ scale factors (a) and resonance frequency offsets (b). The OVS pulse is relatively insensitive to the off-resonance effect due to adiabatic excitation and short tip-back spiral pulse. However, the OVS performance degrades at lower $B_1$ scale factors due to the non-adiabatic tip-back pulse reaching 75% efficiency at a $B_1$ scale factor of 0.6. At a B1 scale factor within 1±0.1 (within 10% of expected), the efficiency was 95%.

Figure 6:
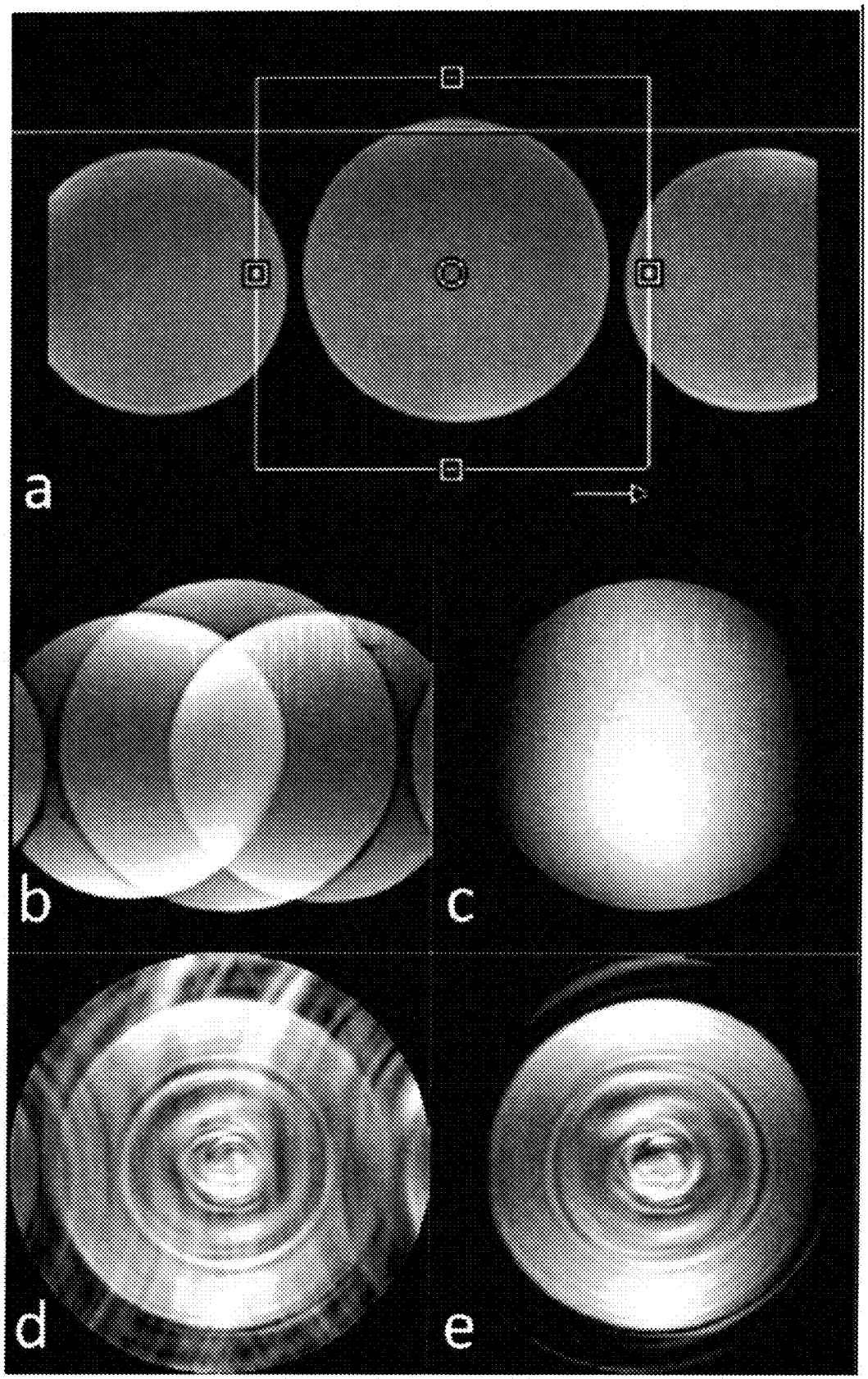
FIG. 6 illustrates OVS performance in phantoms (T1=100 ms) using Cartesian and spiral pulse sequences in accordance with one or more embodiments.

FIG. 6 shows the OVS performance in a phantom using Cartesian and spiral pulse sequences. FIG. 6 at (a) shows the phantom setup along with a yellow-box representing the imaging FOV and an arrow indicating the phase encoding direction for the Cartesian pulse sequence. For the Cartesian sequence without OVS, FIG. 6 at (b), strong spatial aliasing resulted in wrapping artifact. This aliasing was largely suppressed in the Cartesian sequence with OVS (FIG. 6 at (c)). For the highly under-sampled spiral pulse sequence without OVS (FIG. 6 at (d)), the aliasing pattern from the outer phantoms appears as a swirling artifact superimposed on the central water phantom. When the OVS is used with the spiral pulse sequence (FIG. 6 at (e)) the swirling artifacts are dramatically reduced, and the remaining aliasing arises from undersampling of the center water bottle due to the 8× acceleration within the reduced FOV of 170 mm.

Human Studies

Figure 7:
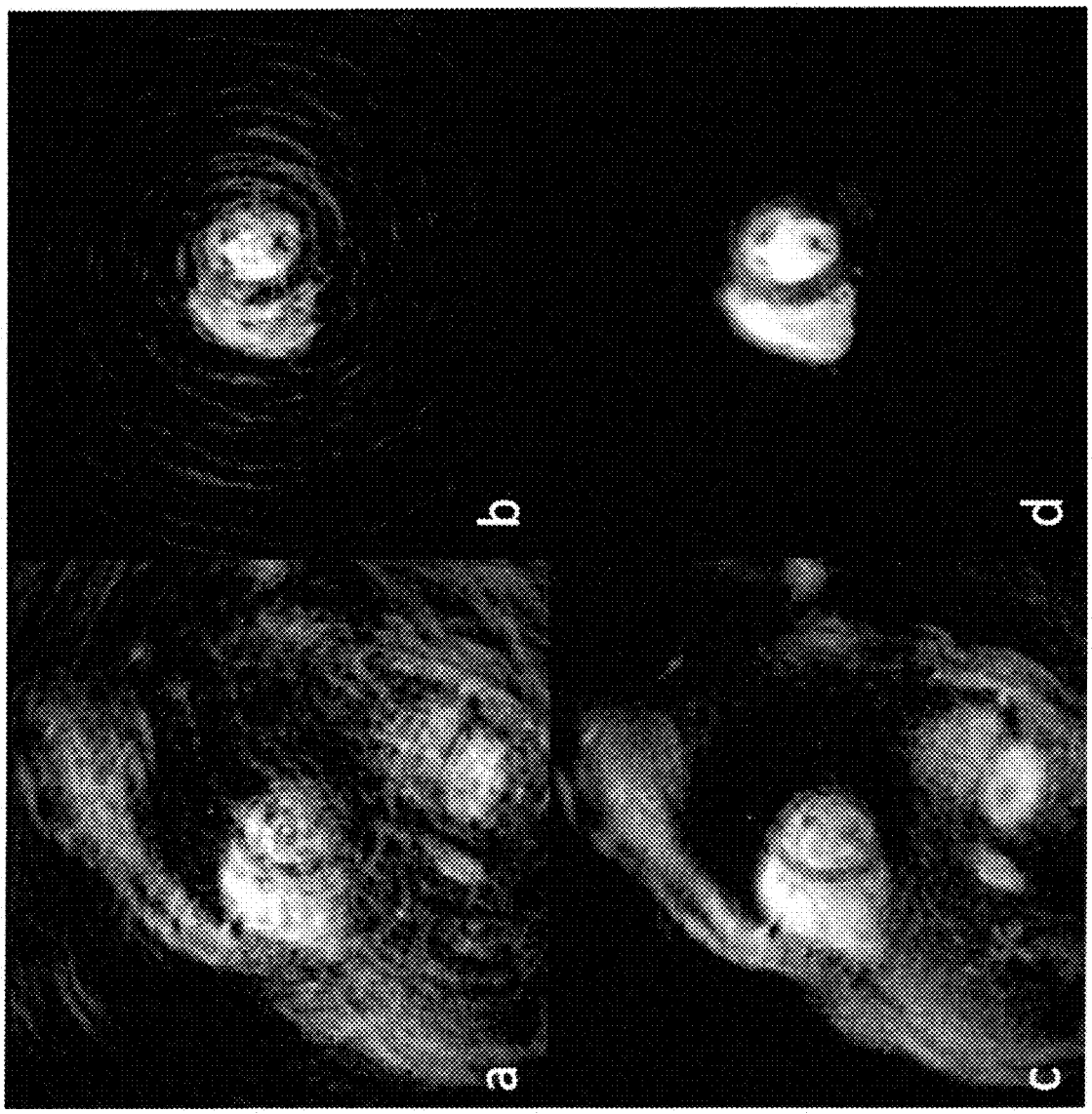
FIG. 7 shows full FOV of 340 mm without OVS (a, c) and rFOV of 170 mm with OVS (b, d) shown in 340 mm FOV perfusion images in accordance with one or more embodiments.

FIG. 7 shows direct reconstruction with zero padding (dc/zp) (a) and BLOSM (c) images from the single-shot spiral sequence with FOV 340 mm without OVS and dc/zp (b) and BLOSM (d) from the single-shot spiral sequence with rFOV 170 mm. As shown, stronger aliasing artifacts are in the direct reconstruction of the data without OVS (a) as compared to the data using the OVS technique (b). Without OVS, the BLOSM technique is not able to completely remove aliasing due to signal from outside of the rFOV of interest (c), whereas in the BLOSM reconstruction with OVS the residual aliasing is removed (d).

Figure 8A:
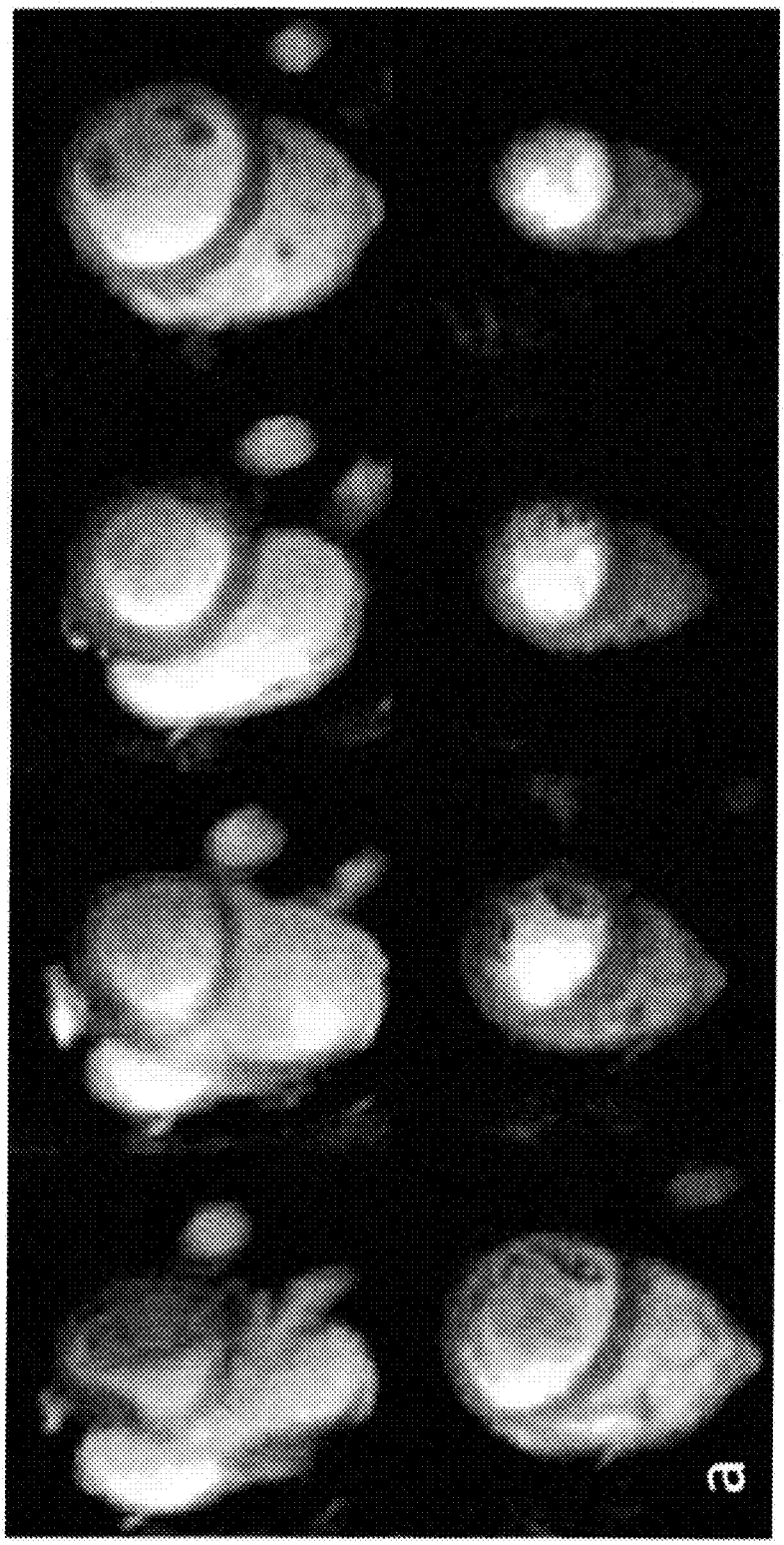
FIGS. 8*a* and 8*b* show resting single-shot OVS spiral perfusion images from a clinical subject, demonstrating high image quality with whole heart coverage and time intensity curves from LV cavity of middle ventricular slice and six averaged segments of myocardium, in accordance with one or more embodiments.
Figure 8B:
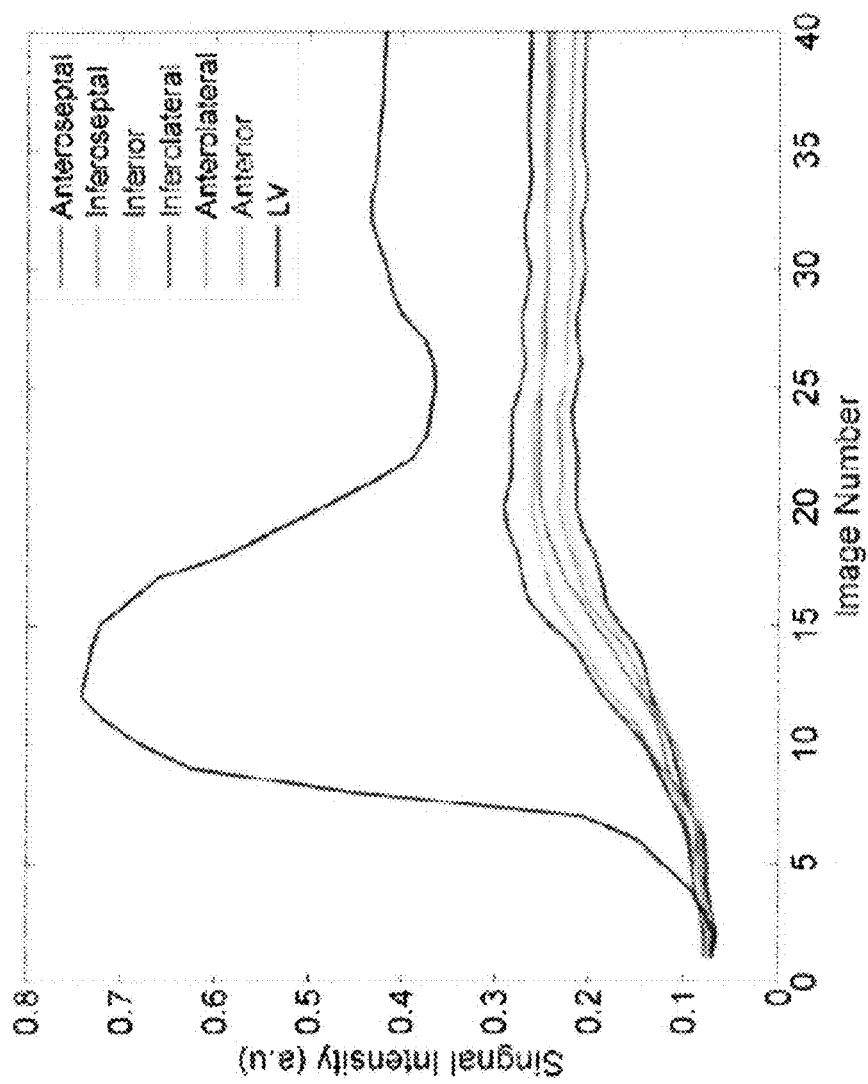

FIG. 8a illustrates the high image quality and whole-ventricle spatial coverage of the single-shot spiral pulse sequence with OVS at a middle time frame during first pass from one subject. The images demonstrate high SNR and image quality with minimal residual aliasing outside the heart region. FIG. 8b shows the time-intensity curves of the LV cavity from a mid-ventricular slice and the time-intensity curves from each myocardial segment averaged across slices. Of the 16 subjects imaged, 12 of the cases had visually apparent respiratory motion present.

Figure 9:
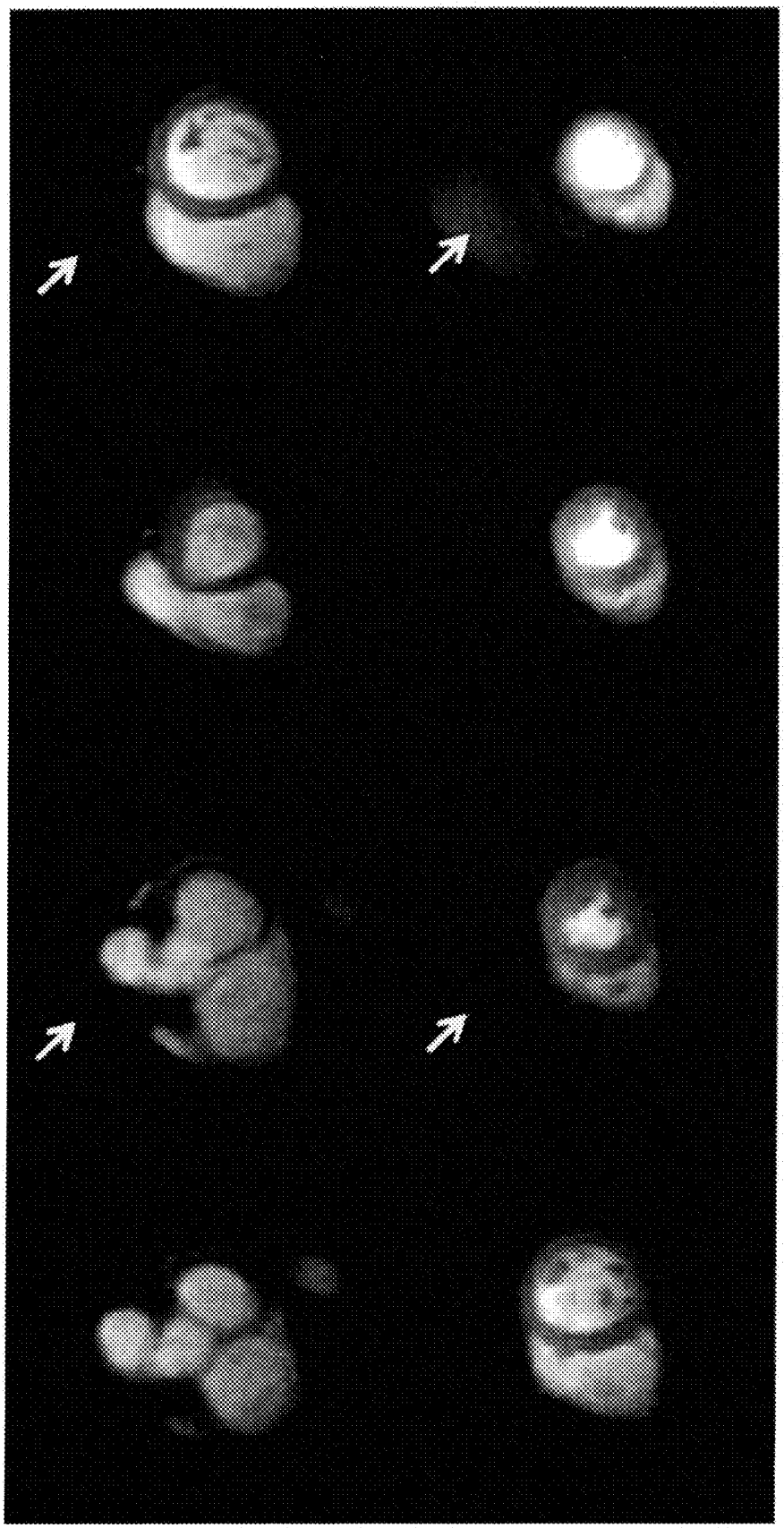
FIG. 9 shows example perfusion images of rFOV to show the different OVS performance of two slices acquired in one SR preparation in accordance with one or more embodiments.

FIG. 9 shows the effect of signal recovery following OVS preparation in a sequence where two slices are acquired per SR preparation. The basal slices which are sampled immediately after the OVS preparation have nearly complete suppression of the outer-volume, whereas images acquired later after the preparation have some recovery of signal. This minimal recovery of signal does not significantly impact image reconstruction quality.

Figure 10:
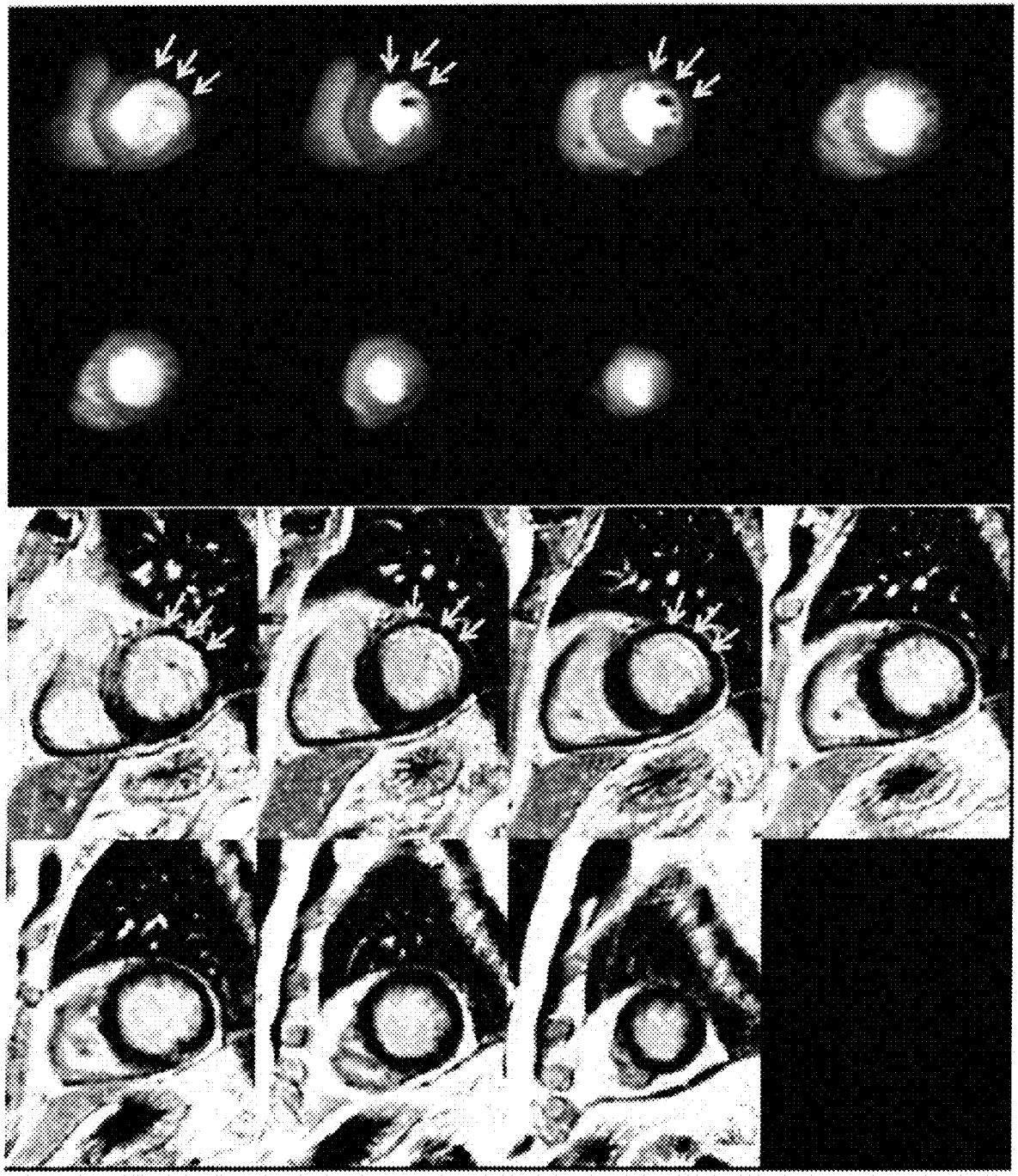
FIG. 10 shows rFOV (170 mm) single-shot perfusion and positive LGE images of a CAD patient in accordance with one or more embodiments.

FIG. 10 shows resting rFOV single-shot spiral perfusion images covering the whole heart from a patient with known CAD. A subendocardial perfusion defect in the anterior and lateral walls corresponded to a region of sub-endocardial myocardial infarction on LGE images. Given the temporal footprint of 8 ms, fine details of the cardiac trabeculations and papillary muscles are evident which are typically not well visualized with other perfusion techniques due to temporal blurring. Four of the patients demonstrated resting perfusion defects which corresponded to regions of scar on LGE imaging.

Average image quality scores (1—excellent, 5—poor) from full FOV cases (N=8) and rFOV cases (N=8) were 3.1±0.64 and 2.3±0.46 (p=0.02) from cardiologist 1, and 2.5±0.54 and 1.8±0.47 (p=0.04) from cardiologist 2. Both cardiologists favored the rFOV image quality as compared to the full FOV images.

Discussion

Reduced FOV spiral perfusion imaging with whole-heart coverage can be achieved by fast 2D OVS preparation combined with a rapid accelerated single-shot spiral pulse sequence resulting in a temporal footprint of <10 ms per slice acquisition. By using an OVS preparation, the signal outside of the desired FOV is significantly attenuated, resulting in reduced aliasing artifacts for the highly-under sampled spiral trajectory. This reduction in aliasing energy significantly improves the BLOSM reconstruction resulting in images of high image quality. The motion correction afforded by BLOSM enables robust image reconstruction even in the setting of respiratory motion. The rFOV spiral perfusion images had higher image quality than the data sets acquired with the full FOV. The circular FOV supported by the spiral tip-back pulse is ideal for spiral acquisition as it provides attenuation of all signals outside of the desired circular FOV.

The rFOV performance is dominated by the OVS module. An adiabatic BIR4 pulse was used to tip-down all spins first and a 2D spiral pulse was applied to tip-back the spins within the ROI. Based on the $B_0$ and $B_1$ simulations, the OVS module is relatively insensitive to the $B_0$ due to the short duration of the tip-back pulse, but the tip-back pulse has some $B_1$ dependence which could result in incomplete tip-back in regions of low $B_1$. Outside of the FOV, there is good suppression of signal which results in minimal aliasing from structures around the heart. Even without complete suppression, attenuation of the signal from outside of the FOV results in significant improvement in image reconstruction. Given the very small temporal footprint of the single-shot spiral readout, multiple slices can easily be acquired following each saturation pulse. The OVS signal recovers with $T_1$ and thus rapid data acquisition is required to ensure the signal outside of the desired FOV has not significantly recovered during readout. Practically, 2-4 slices were acquired following each saturation and OVS preparation with excellent results.

The single-shot spiral acquisition combined with OVS can acquire perfusion image data in under 10 ms per slice at a resolution of 2 mm, which is higher than typically used clinically. The SNR loss of the single readout and thus shorter total data acquisition time as compared to multi-shot spirals is balanced by the utilization of a single 90 degree excitation per slice. With this sequence design, if 4 slices are imaged per SR block, and two SR blocks are used, 8 slices can be acquired in acquired in 240 ms, which is in the range of the temporal footprint of 3D acquisition techniques, but with minimal artifact or blurring due to cardiac motion. This technique may enable whole-heart short-axis coverage even in patients with rapid heart rates such as during exercise, during dobutamine stress, or patients in atrial fibrillation. The high sampling efficiency and the flexibility to control the density of k-space sampling makes spiral trajectories uniquely suited to single-shot image acquisition which has not been achieved for CMR perfusion imaging with any other sampling strategies to date. Collecting the data on a single-spiral interleaf eliminates any potential artifacts which could result from changes in signal intensity or cardiac position between interleaves, and the center of k-space is acquired at a single well-defined SR time.

Perfusion images at two slice locations were acquired after the OVS module within each SR preparation in this study. The first slice was sampled immediately after the OVS resulting in completely suppressed signal outside the ROT. However, the second slice was acquired 10 ms after the OVS module and the magnetization outside the ROT will have recovered a small amount based on the $T_1$ of the surrounding tissues. While long $T_1$ species do not recover significantly over 10 ms, short $T_1$ tissues such as fat the recovery would be about 5% of the total magnetization. This may be optimized by using a tip-down and tip-back pulse greater than 90° to achieve partial inversion in the outer-volume, and with minimal effect on the signal within the rFOV.

Resting perfusion images demonstrate both feasibility of the technique and high image quality. The feasibility of a single-shot spiral perfusion sequence which utilizes OVS and BLOSM CS reconstruction to achieve whole heart perfusion with a very short temporal footprint at any clinically relevant heart rate is demonstrated.

Example 2

Figure 11:
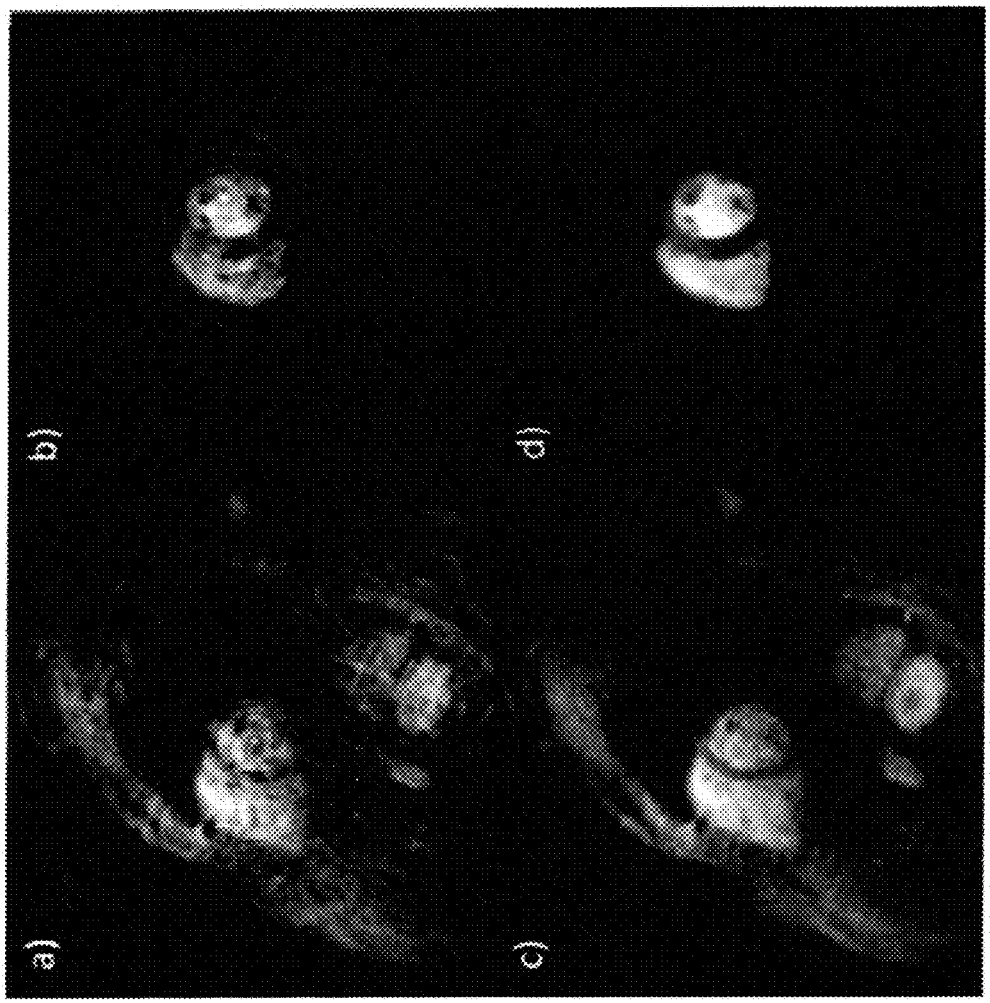
FIG. 11 shows perfusion images from 12× accelerated single-shot spiral with FOV of 340 mm without OVS (a), c)) and with OVS (b), d)). By eliminating the signal around the heart there is reduced aliasing artifact and improved image reconstruction.
Figure 12:
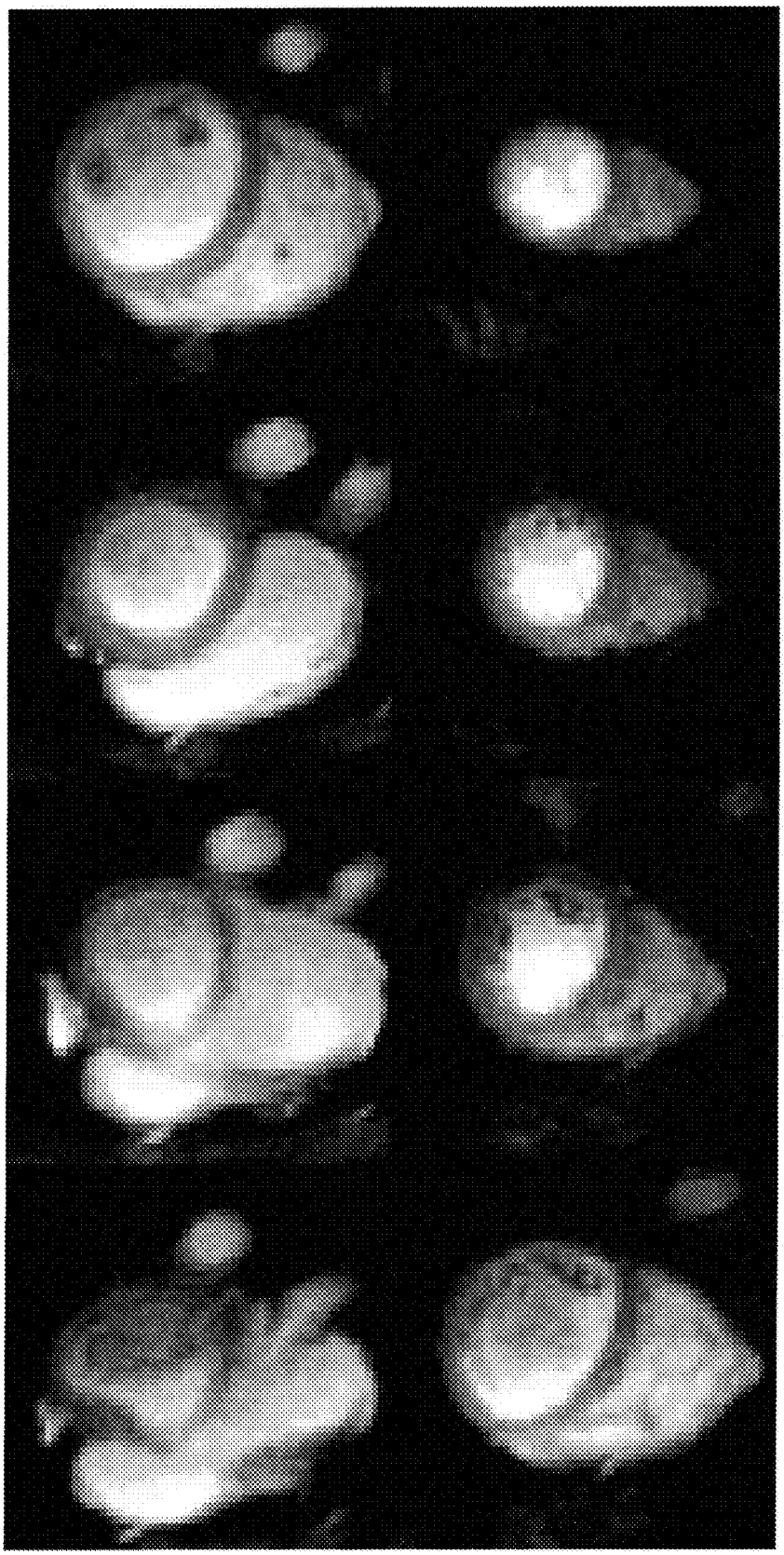
FIG. 12 shows rFOV (170 mm) single-shot spiral perfusion images from a normal subject.
Figure 13:
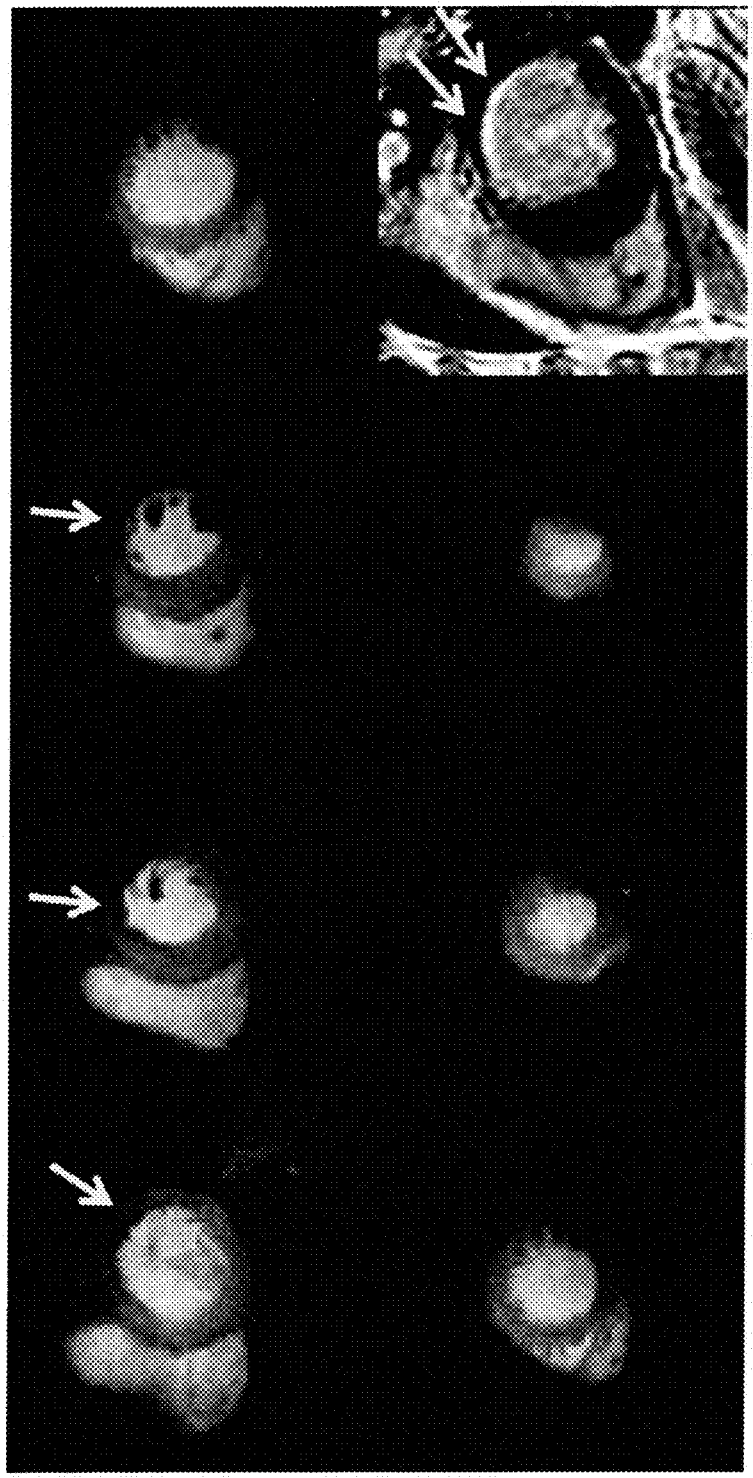
FIG. 13 shows rFOV (170 mm) single-shot spiral perfusion images from a patient with a chronic myocardial infarction. A perfusion defect is seen in the anterior walls (arrows) corresponding the infarct seen on LGE images (bottom right panel).

Another implementation of certain aspects of the present disclosure and discussion of corresponding results will now be described with reference to FIGS. 11-13.

Methods

A rFOV single-shot spiral perfusion pulse sequence using a rapid, B1-robust 2D outer volume suppression (OVS) technique was implemented to enable imaging of a FOV that only includes the heart, as illustrated in FIG. 3. The OVS preparation consisted of a non-selective adiabatic BIR-4 ([25]) tipdown pulse (t=4 ms), a 2D spiral spatial selective ([26]) tipback pulse (t=2.2 ms), and a spoiler (t=2.2 ms) applied during the saturation-recovery preparation to suppress the signal from outside of a cylindrical region around the heart. FIG. 3 illustrates a 2D spiral OVS simulation, according to an embodiment of the present disclosure.

Resting first-pass perfusion was performed in 12 subjects who were undergoing clinically ordered CMR studies with contrast on a 1.5 T Avanto Siemens scanner, using the pulse sequence as described in FIG. 4a.

2 subjects were scanned using FOV 340 mm with highly-accelerated spirals (12× Nyq) with a trajectory start density of 1.2 and an end density of 0.08. 10 subjects of FOV 170 mm with moderately accelerated spirals (6× Nyq) to maintain the same spatial resolution of 2 mm and a trajectory start density of 1.2 and an end density of 0.15. Other sequence parameters included: TE 1.0 ms, TR 9 ms, SRT 80 ms, FA 90°, temporal resolution 8 ms each slice, 2 slices per saturation, and 8 slices to cover the whole myocardium with a 120 mm OVS FOV. The images were reconstructed using Block Low-rank Sparsity with Motion guidance (BLOSM) combined with SENSE.

Results

For the rFOV=100 mm design, the stopband was around ±400 mm, which was large enough to suppress the signals outside of the heart to prevent spatial aliasing. FIG. 11 shows the direct reconstruction (DC) (a) and BLOSM (b) images from 12× accelerated spiral with FOV 340 mm without OVS and DC (c) and BLOSM (d) from same spiral trajectory with OVS. The OVS performed well by limiting signal to the heart region. Without OVS, the aliasing was not completely removed due to the very high accelerated factor needed to support a FOV. FIG. 12 shows rFOV single-shot perfusion images obtained from a normal subject. Only a cylindrical region around the heart was excited. FIG. 13 shows rFOV single-shot spiral perfusion images covering the whole heart from a patient with known CAD. There is a subendocardial perfusion defect in the anterior and lateral walls corresponding to a myocardial infarction on LGE images. Given the temporal footprint of 8 ms, fine details of the cardiac trabeculations and papillary muscles are evident, which are typically not well visualized due to temporal blurring with other perfusion techniques.

Discussion

Spiral tip-back OVS techniques are ideally suited for first-pass perfusion imaging with spiral pulse sequences as they enable a small cylindrical FOV around the heart. The improved sampling efficiency allows for less aggressive spiral acceleration, resulting in higher SNR and reduced residual aliasing artifacts while achieving high spatial/temporal resolution with whole heart coverage. The BLOSM reconstruction enabled motion-insensitive image reconstruction, even in the setting of significant respiratory motion such as free breathing. The 8 ms temporal window for each slice made the imaging insensitive to cardiac motion, producing perfusion images with sharp definition of anatomy.

Example 3

Another implementation of certain aspects of the present disclosure and discussion of corresponding results will now be described with reference to FIGS. 14-16.

Methods

Figure 14:
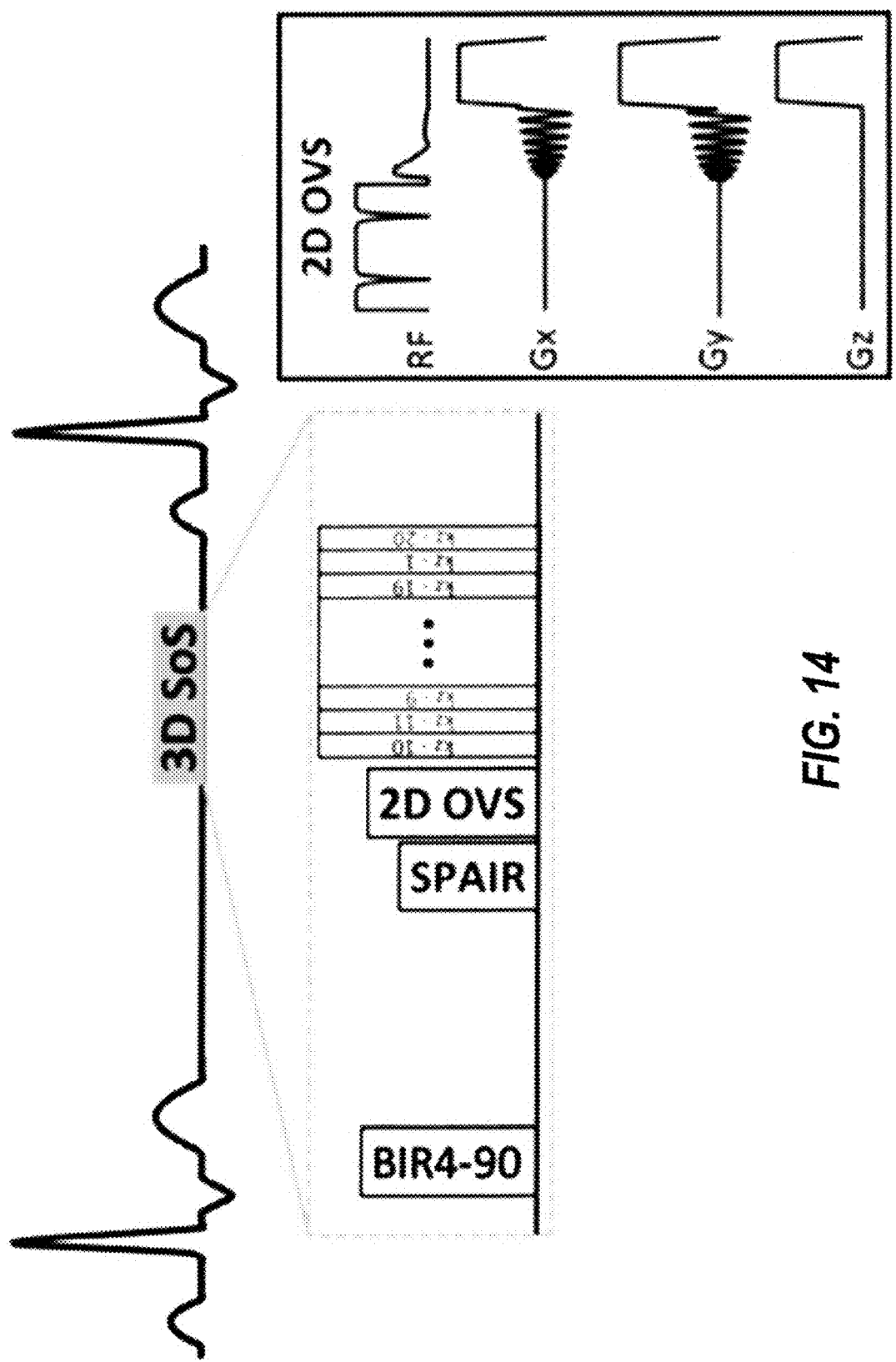
FIG. 14 illustrates a schematic of a rFOV 3D SoS pulse sequence with centric reordering. The inset shows the 2D OVS module consisting of a BIR-4 tip-down pulse and a 2D spiral tip-back pulse as described in FIGS. 3 and 4.

2D OVS preparation was incorporated into a 3D, centrically ordered SoS perfusion sequence, as shown in FIG. 14. The OVS comprised a non-selective adiabatic BIR-4 tipdown pulse, a 2D spiral spatially selective tip-back pulse, and a spoiler to suppress signal outside the heart (as detailed in FIG. 3).

The 3D sequence parameters included: FOV 170×170 mm², TE 1.0 ms, TR 9.0 ms, saturation recovery time 150 ms, flip angle 35°, 2×2 mm in-plane resolution, 20 partitions with 4 mm thickness, 180 ms temporal footprint. For each partition, single 8 ms spiral with a dual density design with a broad Fermi shape transition ([15]) was implemented, and the spiral trajectory was rotated by golden angle through time to generate an incoherent k-t sampling pattern. The proposed sequence was performed in 10 healthy subjects with a 0.075 mmol/kg Gd-DTPA bolus on a 1.5 T Avanto Siemens scanner. The data was reconstructed with two approaches: 1) (thin-slice) 2×2×4 mm with 180 ms temporal footprint; and 2) (high-temporal resolution) 2×2×8 mm with 90 ms temporal footprint using only the central 10 partitions.

BLOSM ([21]) combined with SENSE ([29]) was used for image reconstruction. BLOSM exploits matrix low-rank sparsity within motion-tracked regions from SENSE-combined images. Images were graded on a 5-point scale (5 excellent, 1 poor) by a single cardiologist. 2×2×4 mm data-sets were also interpolated to an isotropic 2×2×2 mm resolution for display in arbitrary image orientations.

Results

Figure 15:
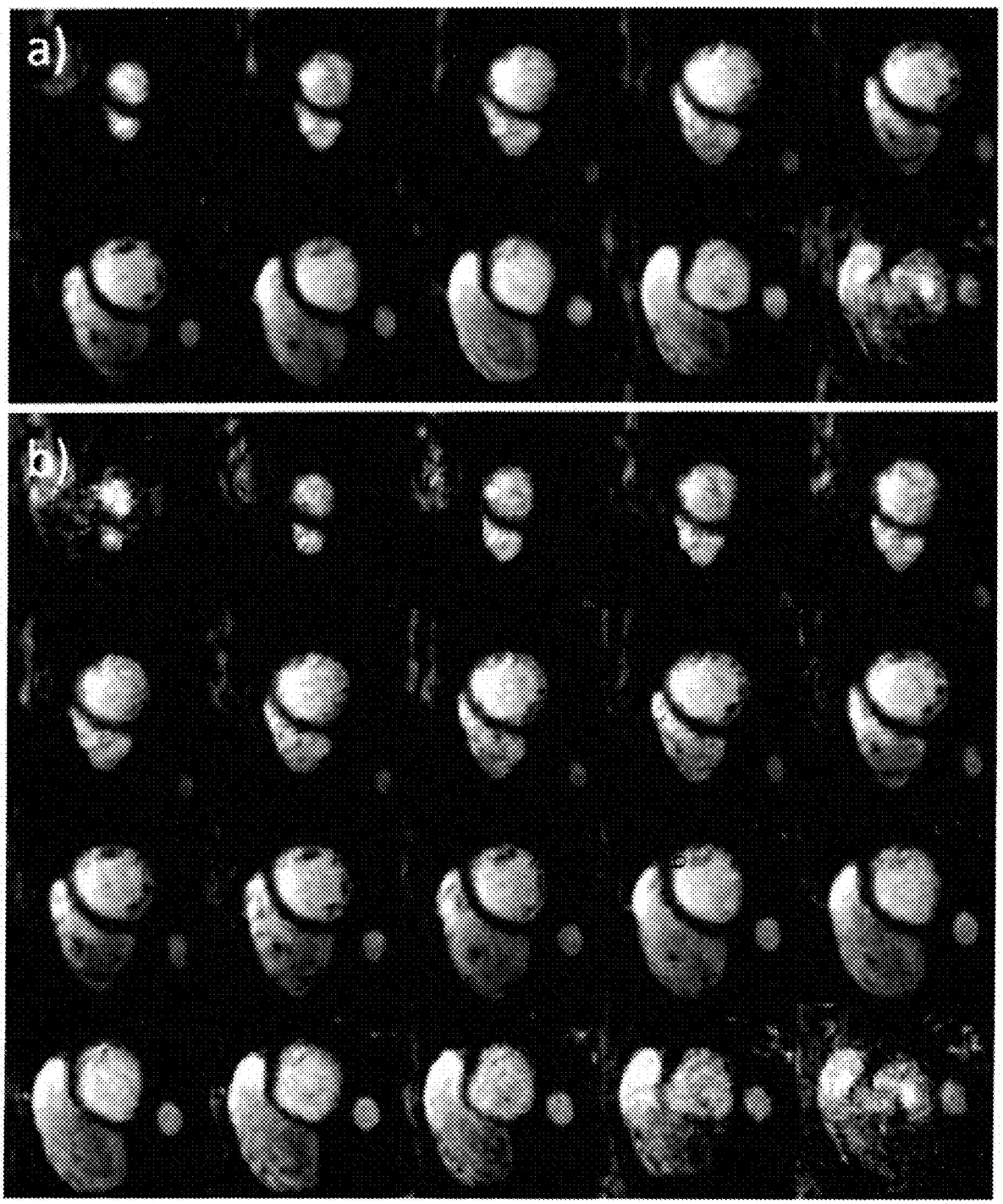
FIG. 15 shows perfusion images from a healthy volunteer with the 3D SoS technique, wherein a) shows 10 slices of 2×2×8 mm resolution with 90 ms temporal footprint and b) shows 20 slices of 2×2×4 mm resolution with 180 ms temporal footprint.
Figure 16:
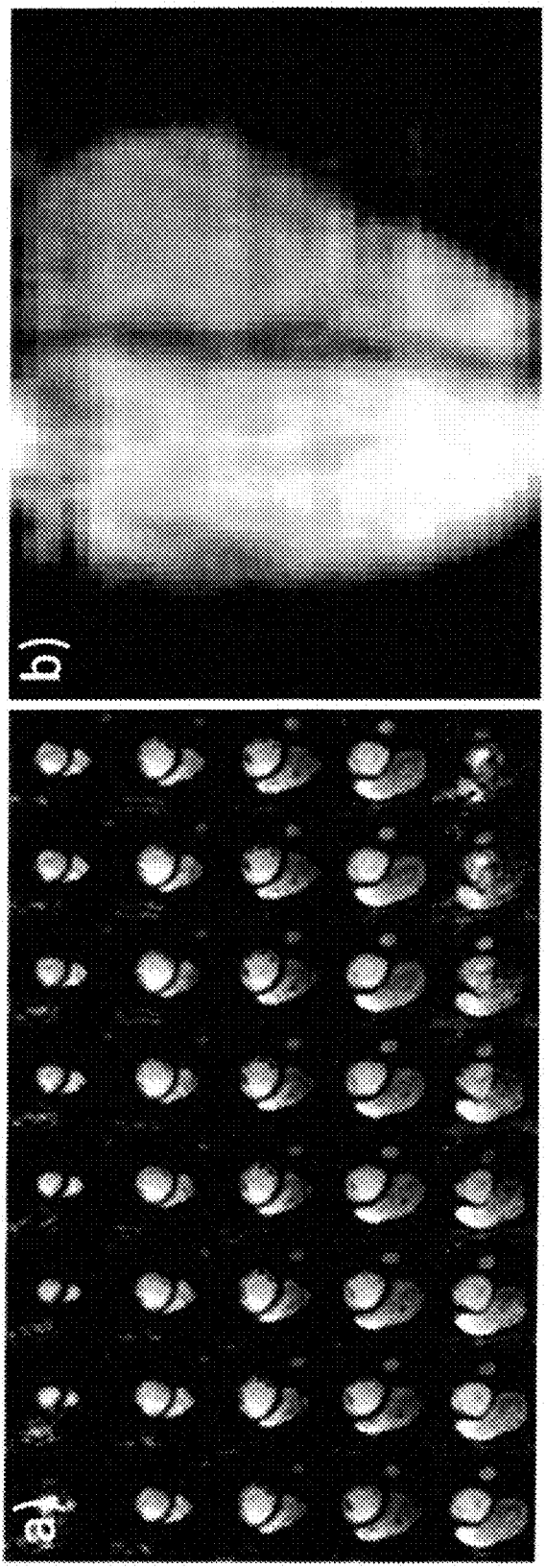
FIG. 16 at a) shows perfusion images wherein data from FIG. 9 is interpolated in the slice direction to display data over 40 slices of 2×2×2 mm resolution with 180 ms temporal footprint, and b) shows long-axis view perfusion images from isotropic resolution images of a).

FIG. 15 shows perfusion images at a single time frame during first-pass of contrast from one healthy volunteer using the 2 different strategies: a) 10 slices with 2×2×8 mm and 90 ms temporal footprint presented high SNR and good quality perfusion images; and b) 20 slices with 2×2×4 mm and 180 ms temporal footprint showed high through-plane resolution images with similar image quality (3.4±0.6 vs 3.6±0.6 p=NS). By 2× sinc-interpolation of the 2×2×4 mm dataset, 40 slices with isotropic 2 mm resolution can be displayed, as shown at FIG. 16, enabling isotropic visualization of perfusion in short and long axis image orientations.

Discussion

OVS enabled high resolution thin-slice (4 mm) 3D perfusion data to be acquired in only 180 ms, while high temporal-resolution 3D data with 8 mm slices can be acquired in only 90 ms. 3D centric reordering allows for a flexible reconstruction strategy to produce either relative higher SNR but lower through-plane resolution (8 mm) perfusion images or lower SNR but higher through-plane (4 mm) resolution. The higher through-plane resolution could reduce partial volume effects and provide better depiction of the apical slices. The isotropic reconstruction provides the ability to reformat the data in arbitrary slice orientations. The short temporal footprint 3D spiral acquisition may have reduced sensitivity to cardiac motion as compared to techniques with a longer temporal footprint resulting in sharper depiction of trabeculae and papillary muscles.

The high sampling efficiency when using OVS enables 3D imaging with an excellent combination of high in-plane and through-plane spatial resolution and a short temporal footprint of 180 ms. The technique can also achieve 3D perfusion coverage with an 8 mm slice thickness in 90 ms, a temporal footprint shorter than most clinically available 2D perfusion pulse sequences. Further validation may be conducted in patients undergoing adenosine stress CMR.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description, and all changes that come within the meaning and range of equivalents thereof are intended to be embraced therein.

REFERENCE LIST

[1] Mozaffarian D, Benjamin E J, Go A S, Arnett D K, Blaha M J, Cushman M, Das S R, de Ferranti S, Despres J P, Fullerton H J, et al. Heart Disease and Stroke Statistics-2016 Update: A Report From the American Heart Association. Circulation. 2016; 133(4):e38-e360.

[2] Salerno M, Beller G A. Noninvasive Assessment of Myocardial Perfusion. Circulation-Cardiovascular Imaging. 2009; 2(5):412-424.

[3] Greenwood J P, Maredia N, Younger J F, Brown J M, Nixon J, Everett C C, Bijsterveld P, Ridgway J P, Radjenovic A, Dickinson C J, et al. Cardiovascular magnetic resonance and single-photon emission computed tomography for diagnosis of coronary heart disease (CE-MARC): a prospective trial. Lancet. 2012; 379(9814): 453-460.

[4] Lipinski M J, McVey C M, Berger J S, Kramer C M, Salerno M. Prognostic value of stress cardiac magnetic resonance imaging in patients with known or suspected coronary artery disease: a systematic review and meta-analysis. J Am Coll Cardiol. 2013; 62(9):826-38.

[5] Jaarsma C, Leiner T, Bekkers S C, Crijns H J, Wildberger J E, Nagel E, Nelemans P J, Schalla S. Diagnostic Performance of Noninvasive Myocardial Perfusion Imaging Using Single-Photon Emission Computed Tomography, Cardiac Magnetic Resonance, and Positron Emission Tomography Imaging for the Detection of Obstructive Coronary Artery Disease A Meta-Analysis. Journal of the American College of Cardiology. 2012; 59(19):1719-1728.

[6] Di Bella E V, Parker D L, Sinusas A J. On the dark rim artifact in dynamic contrast-enhanced MRI myocardial perfusion studies. Magn Reson Med. 2005; 54(5):1295-9.

[7] Manka R, Paetsch I, Kozerke S, Moccetti M, Hoffmann R, Schroeder J, Reith S, Schnackenburg B, Gaemperli O, Wissmann L, et al. Whole-heart dynamic three-dimensional magnetic resonance perfusion imaging for the detection of coronary artery disease defined by fractional flow reserve: determination of volumetric myocardial ischaemic burden and coronary lesion location. Eur Heart J. 2012; 33(16):2016-24.

[8] Manka R, Wissmann L, Gebker R, Jogiya R, Motwani M, Frick M, Reinartz S, Schnackenburg B, Niemann M, Gotschy A, et al. Multicenter Evaluation of Dynamic Three-Dimensional Magnetic Resonance Myocardial Perfusion Imaging for the Detection of Coronary Artery Disease Defined by Fractional Flow Reserve. Circulation-Cardiovascular Imaging. 2015; 8(5).

[9] Jogiya R, Kozerke S, Morton G, De Silva K, Redwood S, Perera D, Nagel E, Plein S. Validation of dynamic 3-dimensional whole heart magnetic resonance myocardial perfusion imaging against fractional flow reserve for the detection of significant coronary artery disease. J Am Coll Cardiol. 2012; 60(8):756-65.

[10] Fair M J, Gatehouse P D, DiBella E V, Firmin D N. A review of 3D first-pass, whole-heart, myocardial perfusion cardiovascular magnetic resonance. J Cardiovasc Magn Reson. 2015; 17:68.

[11] Schwitter J, Nanz D, Kneifel S, Bertschinger K, Buchi M, Knusel P R, Marincek B, Luscher T F, von Schulthess G K. Assessment of myocardial perfusion in coronary artery disease by magnetic resonance: a comparison with positron emission tomography and coronary angiography. Circulation 2001; 103(18):2230-5.

[12] Salerno, Michael; Taylor, Angela; Yang, Yang et al. (2014) Adenosine stress cardiovascular magnetic resonance with variable-density spiral pulse sequences accurately detects coronary artery disease: initial clinical evaluation. Circ Cardiovasc Imaging 2014; 7(4):639-46.

[13] Salerno M, Sica C, Kramer C M, Meyer C H. Improved first-pass spiral myocardial perfusion imaging with variable density trajectories. Magn Reson Med. 2013; 70(5): 1369-79.

[14] Salerno M, Sica C T, Kramer C M, Meyer C H. Optimization of spiral-based pulse sequences for first-pass myocardial perfusion imaging. Magn Reson Med. 2011; 65(6):1602-10.

[15] Yang Y, Kramer C M, Shaw P W, Meyer C H, Salerno M. First-pass myocardial perfusion imaging with whole-heart coverage using L1-SPIRiT accelerated variable density spiral trajectories. Magn Reson Med. 2015.

[16] Luo J, Addy N O, Ingle R R, Hargreaves B A, Hu B S, Nishimura D G, Shin T. Combined outer volume suppression and T preparation sequence for coronary angiography. Magn Reson Med. 2014.

[17] Menon R G, Miller G W, Jeudy J, Rajagopalan S, Shin T. Free breathing three-dimensional late gadolinium enhancement cardiovascular magnetic resonance using outer volume suppressed projection navigators. Magn Reson Med. 2016.

[18] Smith T B, Nayak K S. Reduced field of view MRI with rapid, B1-robust outer volume suppression. Magn Reson Med 2012; 67(5):1316-23.

[19] Tsai C M, Nishimura D G. Reduced aliasing artifacts using variable-density k-space sampling trajectories. Magnetic Resonance in Medicine. 2000; 43(3):452-458.

[20] Staewen R S, Johnson A J, Ross B D, Parrish T, Merkle H, Garwood M. 3-D FLASH imaging using a single surface coil and a new adiabatic pulse, BIR-4. Invest Radiol. 1990; 25(5):559-67.

[21] Chen X, Salerno M, Yang Y, Epstein F H. Motion-compensated compressed sensing for dynamic contrast-enhanced MRI using regional spatiotemporal sparsity and region tracking: block low-rank sparsity with motion-guidance (BLOSM). Magn Reson Med. 2014; 72(4): 1028-38.

[22] Pruessmann K P, Weiger M, Scheidegger M B, Boesiger P. SENSE: sensitivity encoding for fast MRI. Magn Reson Med. 1999; 42(5):952-62.

[23] Walsh D O, Gmitro A F, Marcellin M W. Adaptive reconstruction of phased array M R imagery. Magnetic Resonance in Medicine. 2000; 43(5):682-690.

[24] Combettes P L, Wajs V R. Signal recovery by proximal forward-backward splitting. Multiscale Modeling & Simulation. 2005; 4(4):1168-1200.

[25] Staewen R S, Johnson A J, Ross B D, et al. 3-D FLASH imaging using a single surface coil and a new adiabatic pulse, BIR-4. Invest Radiol 1990; 25:559-67.

[26] Pauly J, Nishimura D, Macovski A. A k-space analysis of small-tip-angle excitation. 1989. J Magn Reson 2011; 213:544-57.

[27] K. P. Pruessmann, M. Weiger, P. Bšrnert, and P. Boesiger, Advances in sensitivity encoding with arbitrary k-space trajectories. Magnetic resonance in medicine, vol. 46, no. 4, pp. 638-51, October 2001.

What is claimed is:

1. A method for magnetic resonance imaging, comprising:
obtaining magnetic resonance imaging (MRI) data for a dynamic series of images corresponding to each of one or more heartbeats of a subject, in a region of interest of the subject that includes the whole heart, and wherein obtaining the MRI data for the dynamic series of images includes acquiring the MRI data using myocardial perfusion imaging that indicates at least blood flow over time in the region of interest,
wherein the acquiring of the MRI data using the myocardial perfusion imaging comprises:
applying an acquisition sequence that uses an under-sampled spiral trajectory configured to thereby increase in-plane spatial resolution and/or reduce temporal footprint and/or increase ventricular coverage, and wherein the obtaining of the MRI data further comprises:
applying a plurality of contrast preparation RF pulses configured to generate a desired image contrast,
applying an outer-volume suppression (OVS) module, prior to acquisition of MRI data for the whole heart, wherein the OVS module is configured to suppress an MRI signal outside the whole heart, and
after application of the OVS module, acquiring the MRI data for the dynamic series of images, wherein the acquiring comprises acquiring multiple slices covering the whole heart for each heartbeat of the one or more heartbeats, and wherein the acquiring is performed for the whole heart before recovery of magnetization from the outer-volume magnetization changes due to T1 recovery in the outer-volume region; and
reconstructing, from the obtained magnetic resonance imaging data, a plurality of reduced field of view (rFOV) magnetic resonance images corresponding to the whole heart.

2. The method of claim 1, wherein the OVS module comprises an outer-volume suppressed 3D stack-of-spirals (SOS) perfusion imaging sequence.

3. The method of claim 1, wherein the outer-volume suppression module comprises outer-volume suppression for single-shot perfusion imaging or interleaved 2D spiral perfusion imaging.

4. The method of claim 1, wherein the magnetic resonance imaging data is acquired along:
a Cartesian trajectory;
a radial trajectory;
an echo-planar trajectory;
a spiral trajectory;
a 2D variant of the Cartesian trajectory, radial trajectory, echo-planar trajectory, or spiral trajectory; or
a 3D variant of the Cartesian trajectory, radial trajectory, echo-planar trajectory, or spiral trajectory.

5. The method of claim 1, wherein acquiring the MRI data uses an imaging pulse sequence that is spin-echo based, gradient-echo based, or a combination thereof.

6. The method of claim 1, wherein the applied contrast preparation RF pulses are configured for T1-weighted or T2-weighted image contrast.

7. The method of claim 1, wherein the image reconstruction is synchronized to each heartbeat of the one or more heartbeats using electrocardiogram (ECG) gating.

8. The method of claim 1, wherein the image reconstruction comprises performing a motion-compensated reconstruction configured to compensate for motion of the subject resulting from cardiac and respiratory motion during the acquisition of the MRI data.

9. The method of claim 1, wherein the in-plane spatial resolution is about 2 mm or less.

10. The method of claim 1, wherein the temporal footprint is about 10 ms or less.

11. A method for magnetic resonance imaging, comprising:
   introducing a T1-shortening contrast agent to a subject; and
   obtaining, using myocardial perfusion imaging, magnetic resonance image (MRI) data for a dynamic series of images corresponding to each of one or more heartbeats of the subject, in a region of interest of the subject that includes the whole heart, wherein the MRI data is obtained while the contrast agent is in the subject in the region of interest and by performing functions that include applying a reduced field of view (rFOV), contrast enhanced myocardial perfusion imaging sequence that indicates at least blood flow over time in the region of interest,
   wherein using the myocardial perfusion imaging comprises:
      applying an acquisition sequence using an under-sampled spiral trajectory with one or more spiral interleaves and an acceleration factor configured to thereby increase in-plane spatial resolution and/or reduce temporal footprint and/or increase spatial coverage,
   wherein the functions further include:
      generating T1 image contrast using a saturation pulse, or a plurality of RF pulses,
      applying a plurality of outer volume suppression (OVS) RF pulses such as to suppress a magnetic resonance imaging (MRI) signal outside of the whole heart, and
      using a 2D or 3D readout module to acquire magnetic resonance imaging data of the subject corresponding to the one or more heartbeats of the subject and the dynamic series of images, wherein the MRI data is acquired after the OVS RF pulses are applied and prior to recovery of magnetization from the outer-volume magnetization changes due to T1 recovery in the outer-volume region.

12. The method of claim 11, further comprising applying additional RF-pulses that are additional to the plurality of RF pulses and configured to selectively suppress a fat signal or excite a water signal associated with the subject.

13. The method of claim 12, wherein the additional RF-pulses comprise spatial-spectral selective pulses.

14. The method of claim 11, wherein an RF pulse of the plurality of RF pulses is used to only excite the MRI signal within the region of interest.

15. The method of claim 11, wherein an RF pulse of the plurality of RF pulses excites or suppresses a cylindrical, rectangular, or arbitrary region of interest.

16. The method of claim 11, wherein the 2D or 3D readout module is gradient echo-based, spin-echo based, or a combination thereof.

17. The method of claim 16, wherein the 2D or 3D readout module comprises echo-train based variants of the gradient echo-based, spin-echo based, or gradient and spin echo-based techniques.

18. The method of claim 11, wherein the magnetic resonance imaging data is acquired along:
   a Cartesian trajectory;
   a radial trajectory;
   an echo-planar trajectory;
   a spiral trajectory;
   a 2D variant of the Cartesian trajectory, radial trajectory, echo-planar trajectory, or spiral trajectory; or
   a 3D variant of the Cartesian trajectory, radial trajectory, echo-planar trajectory, or spiral trajectory.

19. The method of claim 11, wherein multiple slices are excited simultaneously during the readout module.

20. The method of claim 11, comprising the use of a contrast agent which shortens T2 or T2*.

21. The method of claim 11, wherein the preparation RF module is configured to create T2-weighted contrast.

22. The method of claim 11, wherein the preparation RF module uses motion sensitizing gradients with an RF preparation to encode diffusion or myocardial motion.

23. The method of claim 11, wherein the preparation RF module comprises RF pulses configured to achieve magnetization transfer or chemical exchange contrast.

24. The method of claim 11, wherein the dynamic series of images comprises multiple slices of the whole heart of the subject for each heartbeat of the one or more heartbeats.

25. A system for magnetic resonance imaging, comprising:
   a data acquisition device configured to obtain magnetic resonance imaging (MRI) data for a dynamic series of images corresponding to each of one or more heartbeats of a subject, in a region of interest of the subject that includes the whole heart, and wherein obtaining the MRI data for the dynamic series of images includes acquiring the MRI data using myocardial perfusion imaging that indicates at least blood flow over time in the region of interest,
   wherein the acquiring of the MRI data using the myocardial perfusion imaging comprises:
      applying an acquisition sequence that uses an under-sampled spiral trajectory configured to thereby increase in-plane spatial resolution and/or reduce temporal footprint and/or increase ventricular coverage,
   and wherein the obtaining of the MRI data further comprises:
      applying a plurality of contrast preparation RF pulses configured to generate a desired image contrast,
      applying an outer-volume suppression (OVS) module to suppress an MRI signal outside the whole heart, and wherein the OVS module is applied prior to acquisition or MRI data for the whole heart, and
      after application of the OVS module, acquiring the MRI data for the dynamic series of images, wherein the acquiring comprises acquiring multiple slices covering the whole heart for each heartbeat of the one or more heartbeats, and wherein the acquiring is performed for the whole heart before recovery of magnetization from the outer-volume magnetization changes due to T1 recovery in the outer-volume region; and
   one or more processors coupled to the data acquisition device and configured to cause the system to perform functions that comprise:
      reconstructing, from the obtained MRI data, a plurality of reduced field of view (rFOV) magnetic resonance images corresponding to the whole heart.

26. A system for magnetic resonance imaging, comprising:
   a contrast agent source configured to introduce a T1-shortening contrast agent to a subject; and a data acquisition device and one or more processors configured to cause the system to obtain, using myocardial perfusion imaging, magnetic resonance image (MRI) data for a dynamic series of images corresponding to each of one or more heartbeats of the subject, in a region of interest of the subject that includes the whole heart, wherein the MRI data is obtained while the contrast agent is in the subject in the region of interest and by performing functions that include applying a reduced field of view (rFOV), contrast enhanced myocardial perfusion imaging sequence that indicates at least blood flow over time in the region of interest, wherein the obtaining of the MRI data using the myocardial perfusion imaging comprises:

applying an acquisition sequence using an undersampled spiral trajectory with one or more spiral interleaves and an acceleration factor configured to thereby increase in-plane resolution and/or reduce temporal footprint and/or increase spatial coverage, and wherein the functions further include:

generating T1 image contrast using a saturation pulse or a plurality of RF pulses, applying a plurality of outer volume suppression (OVS) RF pulses such as to suppress a magnetic resonance imaging (MRI) signal outside of the whole heart, and using a 2D or 3D readout module to acquire MRI data corresponding to the one or more heartbeats of the subject and the dynamic series of images, wherein the MRI data is acquired after the OVS RF pulses are applied and prior to recovery of magnetization from the outer-volume magnetization changes due to T1 recovery in the outer-volume region.

\* \* \* \* \*